United States Patent
Dejima et al.

(10) Patent No.: US 12,035,891 B2
(45) Date of Patent: Jul. 16, 2024

(54) TREATMENT TOOL, ENDOSCOPE DEVICE, ENDOSCOPE SYSTEM, AND TREATMENT METHOD

(71) Applicant: FUJIFILM Corporation, Tokyo (JP)

(72) Inventors: Takumi Dejima, Waltham, MA (US); Yoshihiro Ueda, Waltham, MA (US)

(73) Assignee: FUJIFILM Corporation, Tokyo (JP)

( * ) Notice: Subject to any disclaimer, the term of this patent is extended or adjusted under 35 U.S.C. 154(b) by 813 days.

(21) Appl. No.: 16/940,367

(22) Filed: Jul. 27, 2020

(65) Prior Publication Data

US 2020/0352422 A1 Nov. 12, 2020

Related U.S. Application Data

(63) Continuation of application No. PCT/JP2019/008886, filed on Mar. 6, 2019.

(Continued)

(51) Int. Cl.
*A61B 1/00* (2006.01)
*A61B 1/005* (2006.01)
(Continued)

(52) U.S. Cl.
CPC ............ *A61B 1/018* (2013.01); *A61B 1/0057* (2013.01); *A61B 1/0661* (2013.01); *A61B 17/29* (2013.01);
(Continued)

(58) Field of Classification Search
CPC ..... A61B 1/018; A61B 1/0057; A61B 1/0661; A61B 17/29; A61B 1/00009;
(Continued)

(56) References Cited

U.S. PATENT DOCUMENTS

| 4,271,845 A | 6/1981 | Chikashige et al. |
| 5,254,130 A | 10/1993 | Poncet et al. |

(Continued)

FOREIGN PATENT DOCUMENTS

| CN | 1636522 | 7/2005 |
| CN | 101579226 | 11/2009 |

(Continued)

OTHER PUBLICATIONS

"Office Action of China Counterpart Application", dated Jan. 5, 2023, with English translation thereof, pp. 1-24.

(Continued)

*Primary Examiner* — Timothy J Neal
*Assistant Examiner* — James Edward Boice
(74) *Attorney, Agent, or Firm* — JCIPRNET

(57) ABSTRACT

An endoscope treatment tool includes an insertion part that is insertable into a first treatment tool channel of an endoscope of an endoscope system, an operation part, and a single operation wire pulled through operation of the operation part. The insertion part includes a distal end portion that has an openable and closable grip portion, a bending portion that is able to be bent, and a connecting-portion that connects the bending portion to the operation part. The connecting-portion is moved forward and backward along a longitudinal axis of the connecting-portion and is rotated about the longitudinal axis. As the connecting-portion is moved forward and backward or is rotated, the grip portion moves forward and backward or rotates, through the operation of the operation part. As the operation wire is pulled, the grip portion is closed, and the bending portion bends in a state where the grip portion is closed.

22 Claims, 41 Drawing Sheets

Related U.S. Application Data

(60) Provisional application No. 62/809,954, filed on Feb. 25, 2019, provisional application No. 62/639,508, filed on Mar. 7, 2018.

(51) Int. Cl.
| | |
|---|---|
| *A61B 1/018* | (2006.01) |
| *A61B 1/06* | (2006.01) |
| *A61B 17/29* | (2006.01) |
| *A61B 17/00* | (2006.01) |
| *A61B 18/14* | (2006.01) |

(52) U.S. Cl.
CPC . *A61B 1/00009* (2013.01); *A61B 2017/00862* (2013.01); *A61B 2017/2927* (2013.01); *A61B 18/1445* (2013.01)

(58) Field of Classification Search
CPC ...... A61B 18/1445; A61B 2017/00862; A61B 2017/2927; A61B 1/00066; A61B 1/0055; A61B 1/0058; A61B 1/005
USPC ......................................................... 600/104
See application file for complete search history.

(56) References Cited

U.S. PATENT DOCUMENTS

| | | | |
|---|---|---|---|
| 6,458,074 B1 | 10/2002 | Matsui et al. | |
| 2003/0076411 A1* | 4/2003 | Iida ........................ | H04N 7/183 |
| | | | 348/E7.087 |
| 2005/0006434 A1 | 1/2005 | Wales et al. | |
| 2005/0119671 A1 | 6/2005 | Reydel et al. | |
| 2006/0189845 A1 | 8/2006 | Maahs et al. | |
| 2008/0154091 A1 | 6/2008 | Dejima et al. | |
| 2009/0287053 A1 | 11/2009 | Okamoto et al. | |
| 2010/0063354 A1 | 3/2010 | Hashimoto et al. | |
| 2012/0022325 A1* | 1/2012 | Hastings ............... | A61B 1/2676 |
| | | | 600/104 |
| 2012/0088968 A1* | 4/2012 | Gambhir ............... | A61M 25/09 |
| | | | 600/106 |
| 2013/0079595 A1 | 3/2013 | Okamoto et al. | |
| 2013/0231534 A1* | 9/2013 | Piskun ............... | A61B 1/00085 |
| | | | 600/114 |
| 2014/0180274 A1* | 6/2014 | Kabaya .............. | A61B 18/1206 |
| | | | 606/34 |
| 2015/0087994 A1 | 3/2015 | Matsuno et al. | |
| 2015/0230697 A1* | 8/2015 | Phee .................... | A61B 1/0057 |
| | | | 901/41 |
| 2016/0231556 A1* | 8/2016 | Yasunaga ........... | G02B 23/2476 |

FOREIGN PATENT DOCUMENTS

| | | |
|---|---|---|
| JP | S558709 | 1/1980 |
| JP | H07505801 | 6/1995 |
| JP | 2001212078 | 8/2001 |
| JP | 2002330927 | 11/2002 |
| JP | 2002330973 | 11/2002 |
| JP | 2008155030 | 7/2008 |
| JP | 2009291414 | 12/2009 |
| WO | 1997012557 | 4/1997 |
| WO | 2014125707 | 8/2014 |

OTHER PUBLICATIONS

"International Search Report (Form PCT/ISA/210) of PCT/JP2019/008886," dated May 21, 2019, with English translation thereof, pp. 1-9.

"Written Opinion of the International Searching Authority (Form PCT/ISA/237) of PCT/JP2019/008886," dated May 21, 2019, with English translation thereof, pp. 1-19.

"The Partial Supplementary Search Report of Europe Counterpart Application", dated Apr. 1, 2021, p. 1-p. 12.

"Office Action of Japan Counterpart Application", dated Mar. 23, 2021, with English translation thereof, p. 1-p. 6.

"Search Report of Europe Counterpart Application", dated Jul. 15, 2021, p. 1-p. 12.

Office Action of China Counterpart Application, with English translation thereof, dated May 18, 2023, pp. 1-18.

"Office Action of China Counterpart Application", dated Sep. 25, 2023, with English translation thereof, pp. 1-19.

* cited by examiner

TREATMENT TOOL, ENDOSCOPE DEVICE, ENDOSCOPE SYSTEM, AND TREATMENT METHOD

This application is a Continuation of PCT International Application No. PCT/JP2019/008886 filed on Mar. 6, 2019, which claims priority under 35 U.S.C § 119(a) to U.S. Provisional Application No. 62/639,508 filed on Mar. 7, 2018, and U.S. Provisional Application No. 62/809,954 filed on Feb. 25, 2019. Each of the above application(s) is hereby expressly incorporated by reference, in its entirety, into the present application.

BACKGROUND OF THE INVENTION

1. Field of the Invention

The present invention relates to a treatment tool, an endoscope device, an endoscope system, and a treatment method.

2. Description of the Related Art

Various types of treatment are performed on a living body by combining an endoscope and a treatment tool. As an example of treatment, endoscopic submucosal dissection (ESD) is known. An inner wall of the esophagus, stomach, and large intestine to which ESD is applied consists of three layers including a mucous membrane layer, a submucosal layer, and a muscular layer. In ESD, a lesion part of the mucous membrane layer including the submucosal layer is peeled off, and it is also possible to collectively excise, for example, a relatively large lesion part which exceeds 2 cm.

An endoscope disclosed in JP2001-212078A is used in, for example, ESD, and comprises a first treatment tool insertion channel and a second treatment tool insertion channel. The first treatment tool insertion channel is open to a distal end of an insertion part of the endoscope, and a first erecting mechanism that erects a treatment tool in a first direction (for example, an up-and-down direction) is provided at a distal end opening portion of the first treatment tool insertion channel. Also the second treatment tool insertion channel is open to the distal end of the insertion part of the endoscope, and a second erecting mechanism that erects the treatment tool in a second direction (for example, a right-and-left direction) different from the first direction is provided at a distal end opening portion of the second treatment tool channel.

In a case where the endoscope disclosed in JP2001-212078A is used, ESD, and a grip forcep is inserted into the first treatment tool insertion channel and an incision tool such as an electric scalpel is inserted into the second treatment tool insertion channel. The grip forcep and an incision tool approach a lesion part from the side of the lesion part along the inner wall. First, as the lesion part is gripped by the grip forcep and the grip forcep gripping the lesion part is erected by the first erecting mechanism, the lesion part is lifted. Then, as a lower part of the lifted lesion part is incised by the incision tool and the incision tool is swung right and left by the second erecting mechanism, incision proceeds. In this manner, the lesion part including the submucosal layer is gradually peeled off.

In addition, also a treatment tool that can perform treatment including both of gripping and incision is known. A treatment tool for an endoscope disclosed in JP2002-330973A comprises a sheath, a forcep member provided at a distal end portion of the sheath, and a high-frequency knife inserted in the sheath. The forcep member is opened and closed by a first operation part provided at a proximal end portion of the sheath. The high-frequency knife protrudes from between a pair of arm portions of the forcep member by a second operation part provided at the proximal end portion of the sheath, and is moved forward and backward in an axial direction of the sheath.

SUMMARY OF THE INVENTION

In the endoscope disclosed in JP2001-212078A, the grip forcep inserted into the first treatment tool insertion channel and the incision tool inserted into the second treatment tool insertion channel are separate treatment tools. As operation of the two treatment tools and operation of the endoscope for erecting each treatment tool are necessary, operation is complicated.

The treatment tool disclosed in JP2002-330973A can only pull the lesion part in the axial direction of the sheath in operation of the treatment tool alone. Bending operation of the endoscope is necessary to lift the lesion part from the side of the lesion part, and the field of view of the endoscope moves in response to the bending operation of the endoscope, thereby increasing the difficulty of treatment. In addition, the high-frequency knife protruding from between the pair of arm portions of the forcep member is directed to the lesion part gripped by the forcep member at all times. For this reason, even in a case where the lesion part is lifted through the bending operation of the endoscope, the high-frequency knife deviates from the lower part of the lesion part, which is an incision target.

In view of circumstances described above, an object of the present invention is to provide a treatment tool, an endoscope device, an endoscope system, and a treatment method that allow safe, reliable, and easy performance of lifting of a lesion part, exposing a part, which is a treatment target, so as to be easily visible by lifting the lesion part, and accordingly another treatment respect to a part to be treated.

According to an aspect of the present invention, there is provided a treatment tool comprising an insertion part that is insertable into a body, an operation part, a single operation wire that extends from the operation part to the insertion part and is pulled to an operation part side through operation of the operation part. The insertion part includes a distal end portion that has an openable and closable grip portion, a bending portion that is provided to be adjacent to the operation part side of the distal end portion and is able to be bent, and a connecting portion that connects the bending portion to the operation part. The connecting portion is moved forward and backward along a longitudinal axis of the connecting portion and is rotated about the longitudinal axis of the connecting portion, through the operation of the operation part. As the connecting portion is moved forward and backward or is rotated, the grip portion moves forward and backward or rotates. As the operation wire is pulled, the grip portion is closed, and the bending portion bends in a state where the grip portion is closed.

According to another aspect of the present invention, there is provided a treatment tool comprising an insertion part that is insertable into a body and an operation part. The insertion part includes a distal end portion that has a grip portion which is opened and closed through operation of the operation part, a bending portion that is provided to be adjacent to an operation part side of the distal end portion and bends through the operation of the operation part, and a connecting portion that connects the bending portion to the operation part. The connecting portion has a pipe line, into which another endoscope treatment tool is insertable, therein. The bending portion has a pipe line outlet that communicates with the pipe line and is open to an outer peripheral surface of the bending portion.

According to still another aspect of the present invention, there is provided an endoscope device comprising a first treatment tool that is the treatment tool described above, a second treatment tool, and an endoscope that has a first treatment tool channel into which the first treatment tool is insertable and a second treatment tool channel into which the second treatment tool is insertable.

According to still another aspect of the present invention, there is provided an endoscope device comprising a first treatment tool that is the treatment tool described above, a second treatment tool, an endoscope that has a treatment tool channel into which one treatment tool of the first treatment tool or the second treatment tool is insertable, and a guide sheath that has a treatment tool channel into which the other treatment tool of the first treatment tool or the second treatment tool is insertable and an endoscope channel into which the endoscope is insertable.

According to still another aspect of the present invention, there is provided an endoscope device comprising a first treatment tool that is the treatment tool described above, a second treatment tool that is insertable into the pipe line of the first treatment tool, and an endoscope that comprises a treatment tool channel into which the first treatment tool is insertable.

According to still another aspect of the present invention, there is provided an endoscope system comprising the endoscope device, a light source device that supplies illumination light to the endoscope of the endoscope device, and a processor that processes an image signal output from the endoscope.

According to still another aspect of the present invention, there is provided a treatment method comprising disposing the distal end portion of the first treatment tool at a lesion part in a body through the first treatment tool channel of the endoscope, gripping the lesion part by the grip portion of the first treatment tool, lifting, in a state where the lesion part is gripped, the lesion part by bending the bending portion of the first treatment tool, and treating, in a state where the lesion part is lifted, a lower part of the lesion part by the second treatment tool inserted in the second treatment tool channel of the endoscope.

According to still another aspect of the present invention, there is provided a treatment method comprising disposing the distal end portion of the first treatment tool at a lesion part in a body through one treatment tool channel of the treatment tool channel of the endoscope or the treatment tool channel of the guide sheath, gripping the lesion part by the grip portion of the first treatment tool, lifting, in a state where the lesion part is gripped, the lesion part by bending the bending portion of the first treatment tool, and treating, in a state where the lesion part is lifted, a lower part of the lesion part by the second treatment tool inserted in the other treatment tool channel of the treatment tool channel of the endoscope or the treatment tool channel of the guide sheath.

According to still another aspect of the present invention, there is provided a treatment method comprising disposing the distal end portion of the first treatment tool at a lesion part in a body through the treatment tool channel of the endoscope, gripping the lesion part by the grip portion of the first treatment tool, lifting, in a state where the lesion part is gripped, the lesion part by bending the bending portion of the first treatment tool, and treating, in a state where the lesion part is lifted, a lower part of the lesion part by the second treatment tool inserted in the pipe line of the first treatment tool.

In the present invention, it is possible to provide a treatment tool, an endoscope device, an endoscope system, and a treatment method that allow safe, reliable, and easy performance of lifting of a lesion part, exposing a part, which is a treatment target, so as to be easily visible by lifting the lesion part, and accordingly another treatment respect to the part to be treated.

DESCRIPTION OF THE PREFERRED EMBODIMENTS

Figure 1:
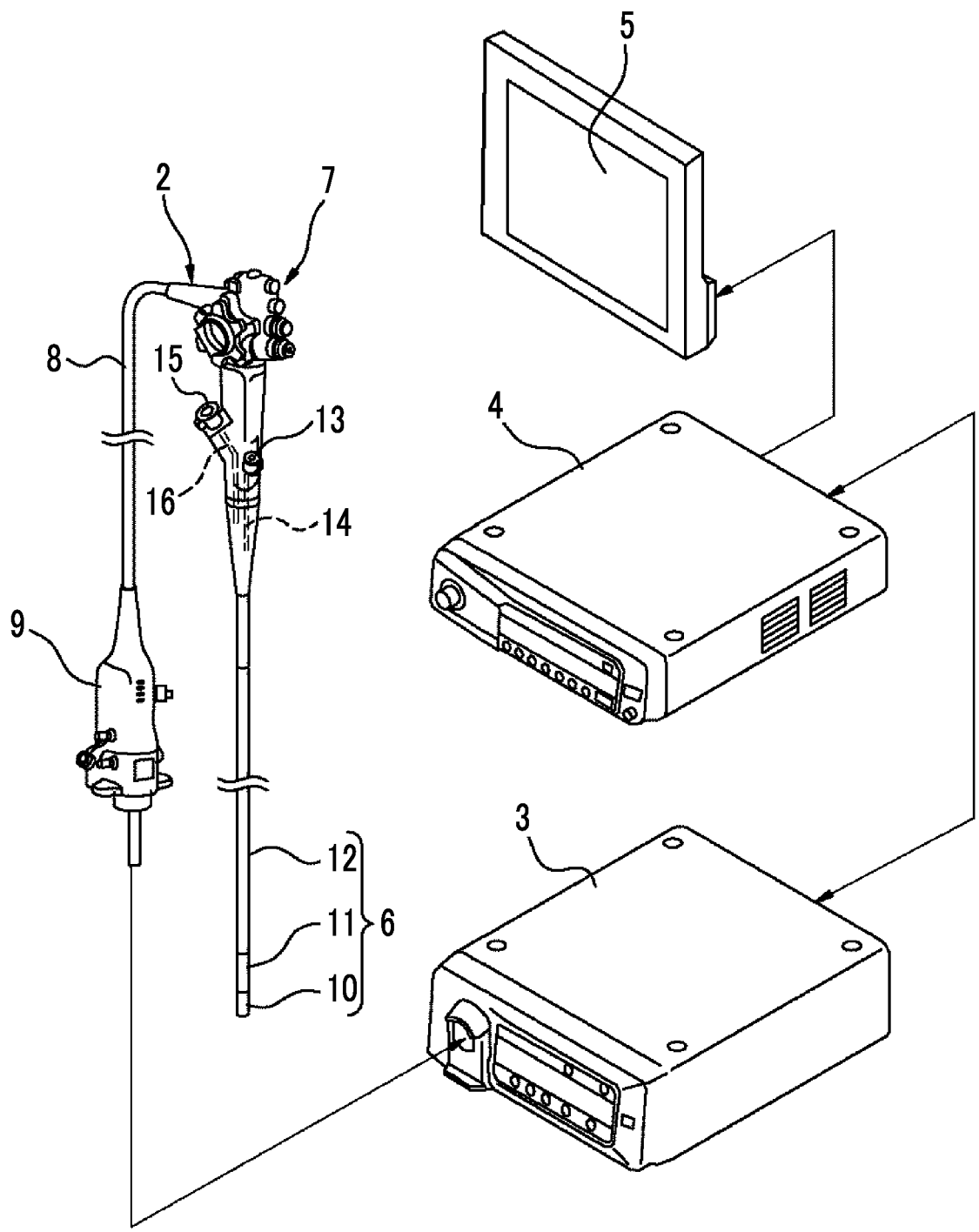
FIG. 1 is a view illustrating an example of an endoscope system, which is for describing an embodiment of the present invention.

FIG. 1 illustrates an example of an endoscope system for describing an embodiment of the present invention.

An endoscope system 1 comprises an endoscope 2, a light source device 3, and a processor 4. The endoscope 2 has an endoscope insertion part 6 that is inserted into a subject, an endoscope operation part 7 that is connected to the endoscope insertion part 6, and a universal cord 8 that extends from the endoscope operation part 7. The endoscope insertion part 6 is configured by an endoscope distal end portion 10, an endoscope bending portion 11 that is connected to the endoscope distal end portion 10, and an endoscope connecting portion 12 that connects the endoscope bending portion 11 to the endoscope operation part 7.

An image pick-up device including an imaging element is mounted on the endoscope distal end portion 10. The endoscope bending portion 11 is configured to be able to be bent, and the bending of the endoscope bending portion 11 is operated by the endoscope operation part 7. In addition, the endoscope connecting portion 12 is configured to be flexible so as to be deformable along a shape of an insertion passage in the subject.

The endoscope operation part 7 is provided with an operation button for operating image pick-up using the image pick-up device and an operation knob for operating the bending of the endoscope bending portion 11. In addition, the endoscope operation part 7 is provided with a first treatment tool insertion opening 13 and a second treatment tool insertion opening 15, into which an endoscope treatment tool is insertable. Inside the endoscope insertion part 6, a first treatment tool channel 14 that reaches the endoscope distal end portion 10 from the first treatment tool insertion opening 13 and is open to an end surface of the endoscope distal end portion 10 and a second treatment tool channel 16 that reaches the endoscope distal end portion 10 from the second treatment tool insertion opening 15 and is open to the end surface of the endoscope distal end portion 10 are provided.

A light guide and a cable are provided inside the endoscope insertion part 6, the endoscope operation part 7, and the universal cord 8. A connector 9 is provided at a terminal of the universal cord 8. The endoscope 2 is connected to the light source device 3 and the processor 4 via the connector 9.

Illumination light generated by the light source device 3 is guided to the endoscope distal end portion 10 via the light guide and is emitted from the endoscope distal end portion 10. In addition, operating power of the imaging element, a control signal for driving the imaging element, and an image signal output from the imaging element are transmitted between the processor 4 and the image pick-up device via the cable. The processor 4 processes the input image signal to generate image data of an observed part in the subject, displays the generated image data on a monitor 5, and records the generated image data.

Figure 2:
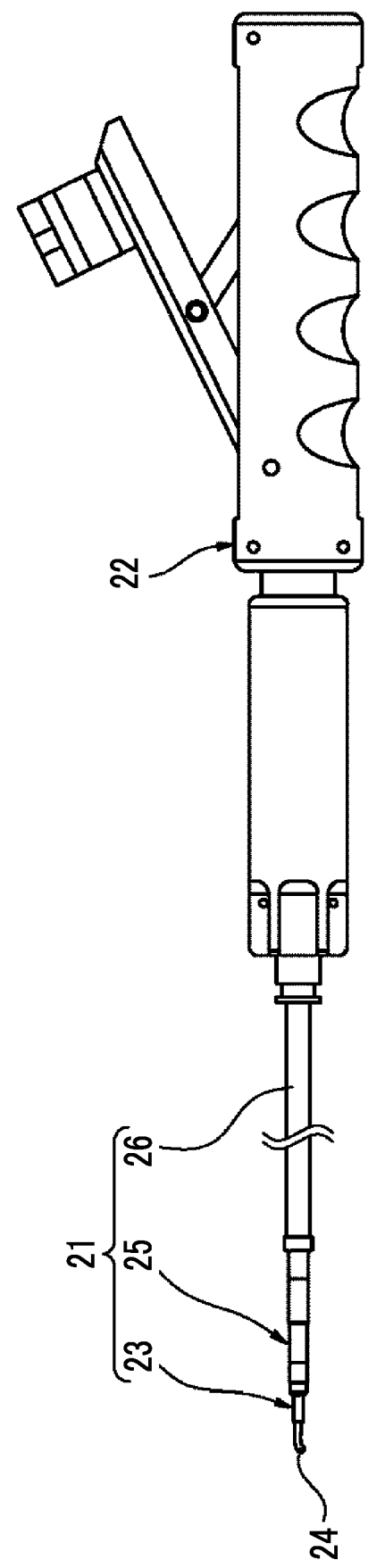
FIG. 2 is a view illustrating an example of an endoscope treatment tool, which is for describing the embodiment of the present invention.

FIG. 2 illustrates an example of the endoscope treatment tool, which is for describing the embodiment of the present invention.

An endoscope treatment tool 20 comprises an insertion part 21 that is insertable into the first treatment tool channel 14 (refer to FIG. 1) and an operation part 22. The insertion part 21 includes a distal end portion 23 that has a grip portion 24 which is operated to be opened and closed by the operation part 22, a bending portion 25 that is provided to be adjacent to an operation part side of the distal end portion 23, and a connecting portion 26 that connects the bending portion 25 to the operation part 22.

In a case where the insertion part 21 is inserted in the first treatment tool channel 14, the distal end portion 23 and the bending portion 25 protrude from the end surface of the endoscope distal end portion 10 (refer to FIG. 1), and the connecting portion 26 is accommodated in the first treatment tool channel 14. Similar to the endoscope connecting portion 12, the connecting portion 26 accommodated in the first treatment tool channel 14 is configured to be flexible so as to be deformable along the shape of the insertion passage in the subject.

Figure 3:
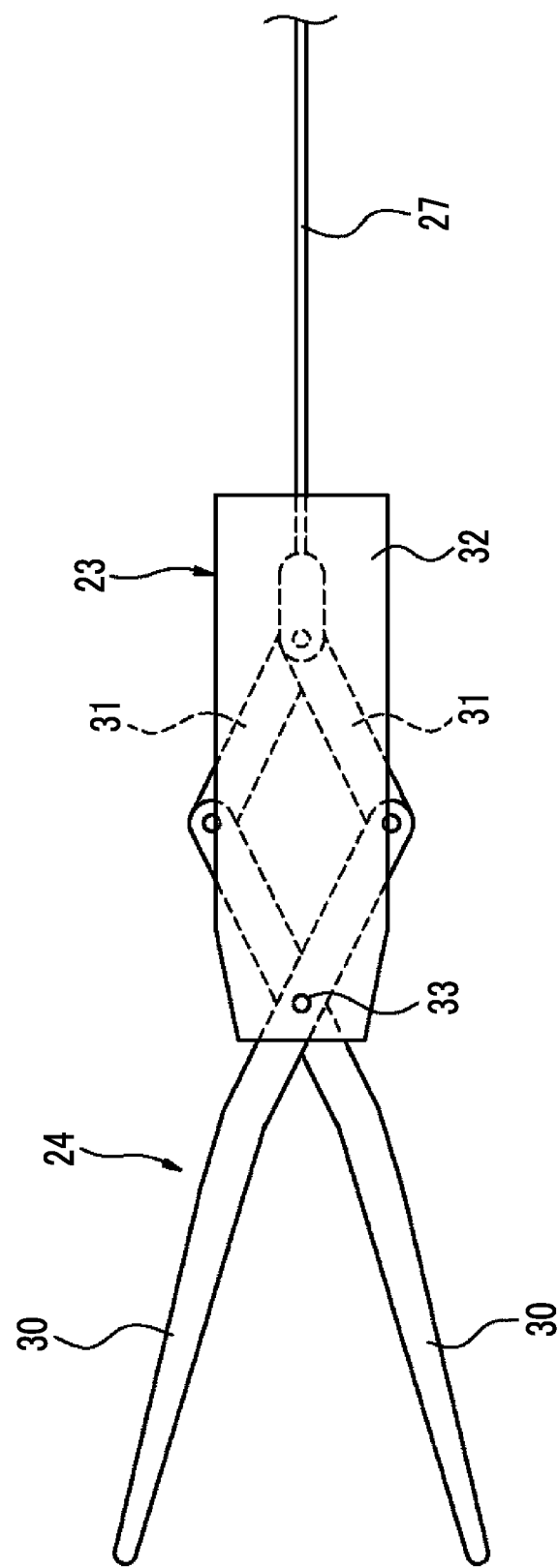
FIG. 3 is a view illustrating a configuration of a grip portion of a distal end portion of the endoscope treatment tool of FIG. 2.
Figure 4:
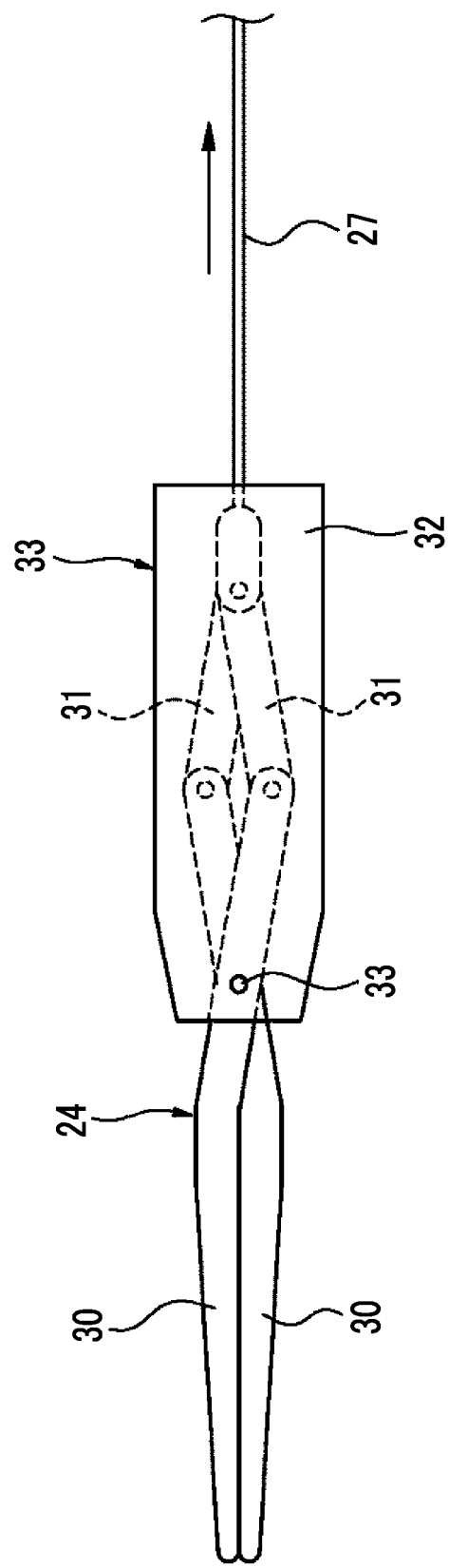
FIG. 4 is a view illustrating an operation of the grip portion of FIG. 3.

FIGS. 3 and 4 illustrate a configuration and an operation of the grip portion 24 of the distal end portion 23.

In the example illustrated in FIG. 3, the grip portion 24 has a pair of grip claws 30 and a pair of link members 31, and the distal end portion 23 has a support body 32 that supports the pair of grip claws 30 so as to be movable rotationally. The pair of grip claws 30 are disposed to intersect each other, and a pin 33 is provided to penetrate an intersecting portion of the pair of grip claws 30. The pin 33 is fixed to the support body 32, and the grip claws 30 are supported by the support body 32 so as to be movable rotationally about the pin 33 which is a rotation axis.

Distal end portions of the link members 31 are connected to proximal end portions of the grip claws 30 so as to be movable rotationally, and an operation wire 27 is connected to proximal end portions of the link members 31. The operation wire 27 reaches the operation part 22 from the distal end portion 23 via the bending portion 25 and the connecting portion 26, and is pulled to an operation part 22 side or is pushed out to a distal end portion 23 side in response to operation of the operation part 22.

FIG. 3 illustrates a state where the operation wire 27 is pushed out to the distal end portion 23 side, and distal end portions of the pair of grip claws 30 are open. As the operation wire 27 is pulled to the operation part 22 side, the distal end portions of the pair of grip claws 30 are closed as illustrated in FIG. 4. A part to be treated of a living body is gripped by the distal end portions of the pair of closed grip claws 30.

Figure 5:
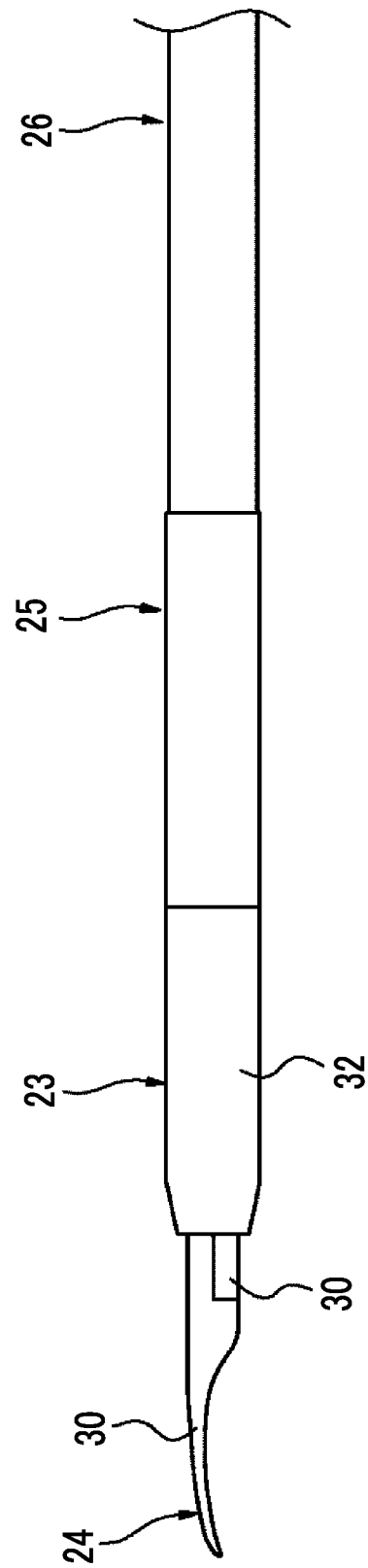
FIG. 5 is a view illustrating configurations of a bending portion and a connecting portion of the endoscope treatment tool of FIG. 2.
Figure 6:
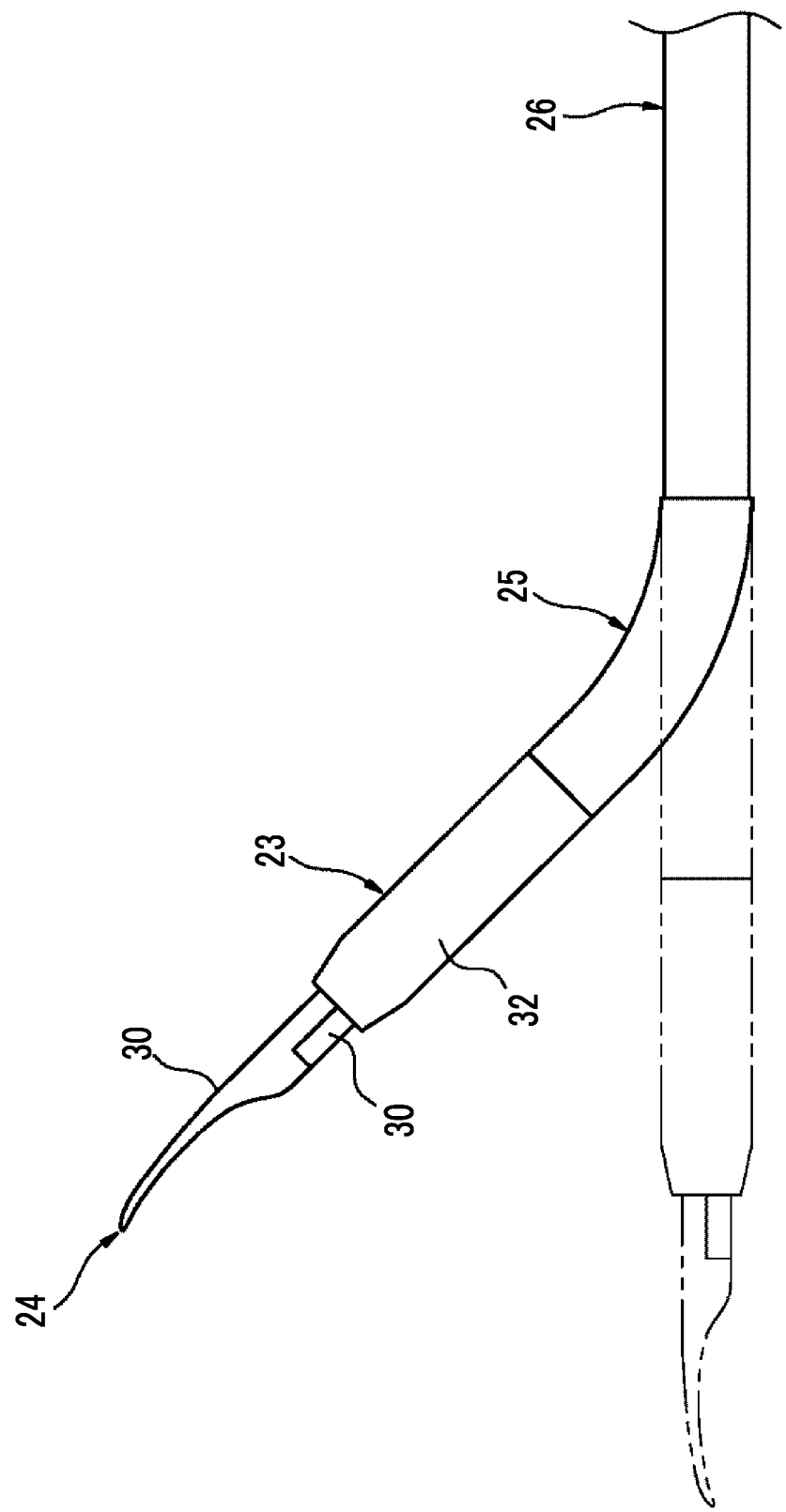
FIG. 6 is a view illustrating an operation of the bending portion of FIG. 5.

FIGS. 5 and 6 illustrate configurations and operations of the bending portion 25 and the connecting portion 26.

The connecting portion 26 has flexibility and also has stiffness that allows translational and rotational power to be transmitted from the operation part 22 side to a bending portion 25 side. Such a connecting portion 26 can be configured, for example, such that an outer periphery of a screw pipe, which is formed by spirally winding a metal strip plate material, is covered with a mesh pipe formed by braiding a metal wire and an outer periphery of the mesh pipe is covered with a resin outer coat. As illustrated in FIG. 6, the bending portion 25 is able to be bent in a direction substantially perpendicular to an opening and closing direction of the pair of grip claws 30 and is operated to be bent by the operation part 22.

Figure 7:
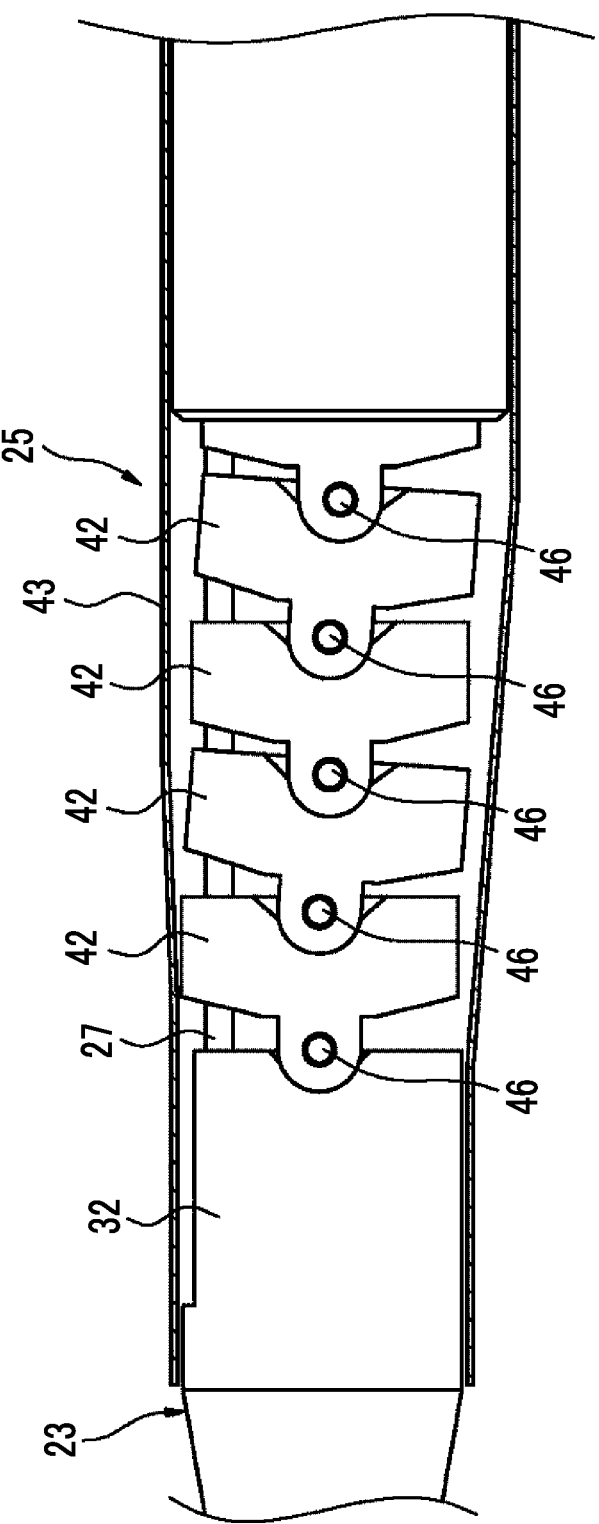
FIG. 7 is a view illustrating a configuration of an inside of the bending portion of FIG. 5.
Figure 8:
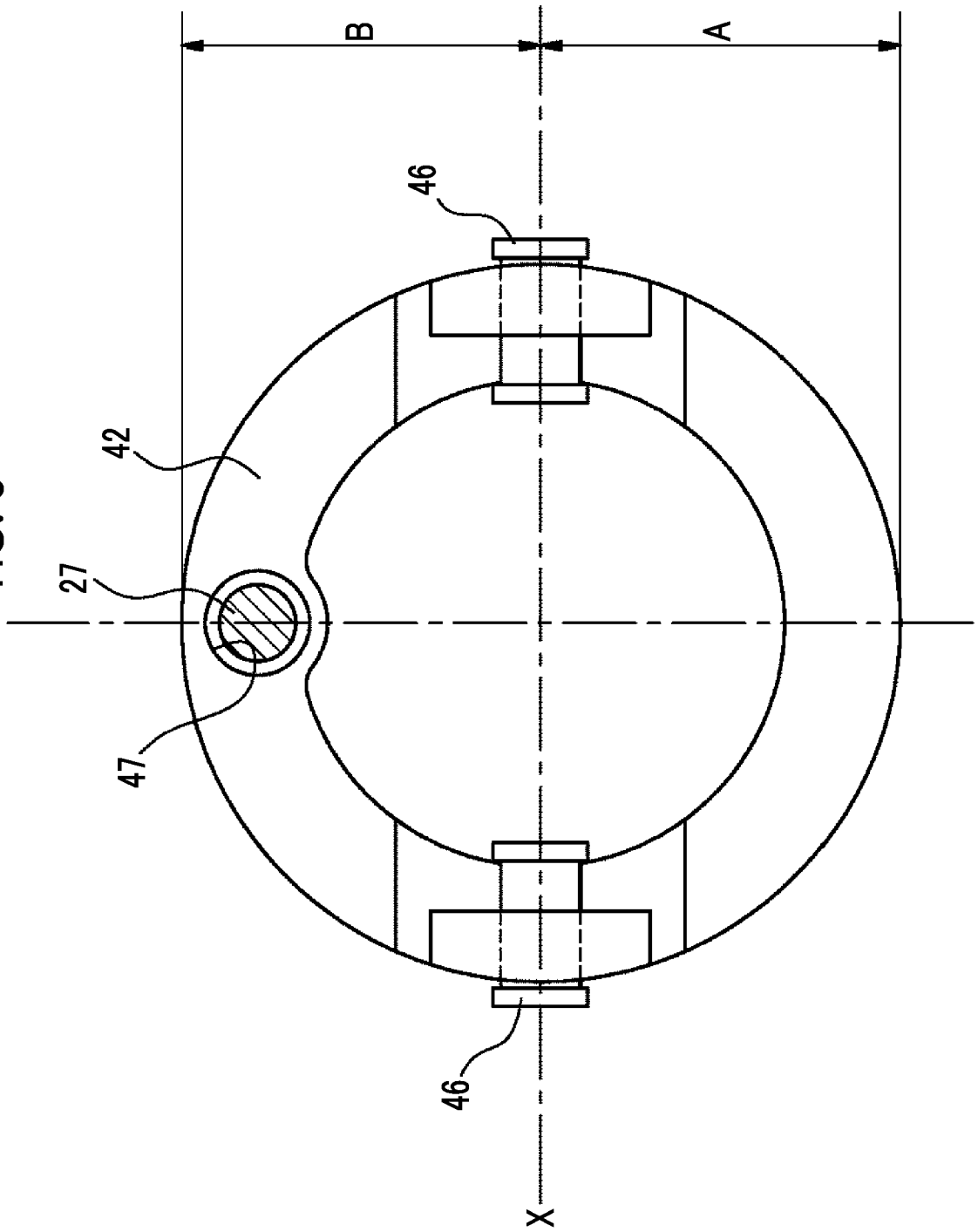
FIG. 8 is a view illustrating the configuration of the inside of the bending portion of FIG. 5.
Figure 9:
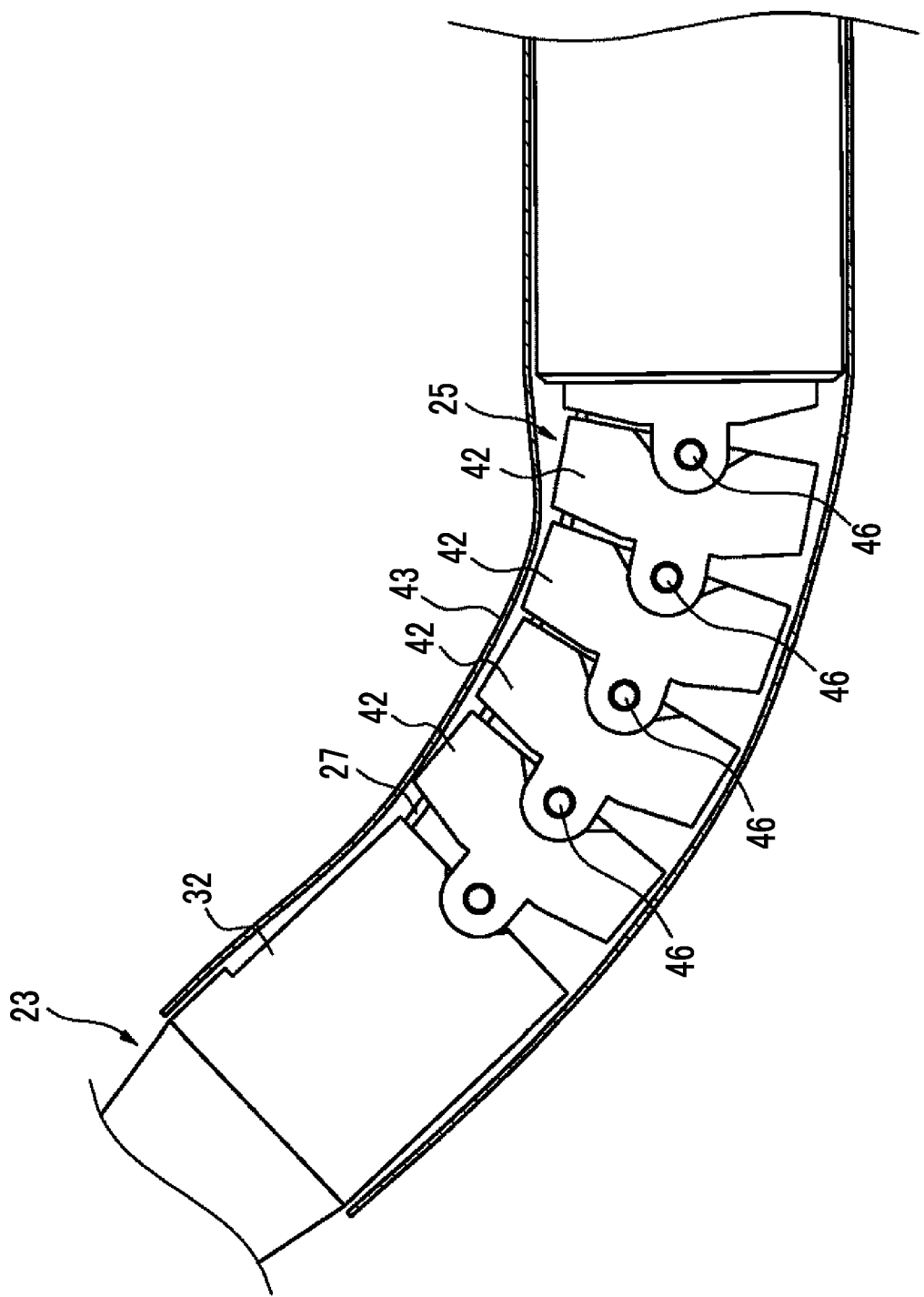
FIG. 9 is a view illustrating an operation inside the bending portion of FIG. 5.

FIGS. 7 to 9 illustrate a configuration and an operation of the inside of the bending portion 25.

The bending portion 25 has a plurality of bending pieces 42 and a resin outer coat 43. The plurality of bending pieces 42 are disposed to be arranged in a longitudinal direction of the insertion part 21 including the bending portion 25. Two adjacent bending pieces 42 are connected to each other via a pair of pins 46. The pair of pins 46 are disposed on an axis X that is substantially parallel to the opening and closing direction of the pair of grip claws 30, and the two bending pieces 42 connected to each other by the pair of pins 46 are movable rotationally about the axis X which is a rotation axis. By adding rotational movements of the plurality of bending pieces 42 about the axis X which is a rotation axis, the bending portion 25 bends in the direction substantially perpendicular to the opening and closing direction of the pair of grip claws 30 as illustrated in FIG. 9.

The bending portion 25 is bent by the operation wire 27 for opening and closing the pair of grip claws 30. Each of the plurality of bending pieces 42 has a wire guide 47 that holds the operation wire 27 in a pushable and pullable manner. In a case where each of the bending pieces 42 is divided into two sides including a first side A and a second side B, which is an opposite side, with the axis X as a boundary, the wire guide 47 is provided on one side, which is the second side B. As the operation wire 27 is pulled to the operation part 22 side, the bending portion 25 is bent such that the first side A is positioned outside the curve and the second side B is positioned inside the curve.

In this manner, a closing operation of the grip portion 24 and a bending operation of the bending portion 25 are performed by pulling the single operation wire 27. Accordingly, operation of the operation part 22 is easy. Herein, in a case where the operation wire 27 is pulled to the operation part 22 side, the grip portion 24 is first closed, and the bending portion 25 is configured to bend in a state where the grip portion 24 is closed. An operation sequence of the closing operation of the grip portion 24 and the bending operation of the bending portion 25 can be set depending on a relationship as to which one of an operation resistance in a case where the grip portion 24 is closed or an operation resistance in a case where the bending portion 25 bends is larger or smaller. In a case where the operation resistance of the bending portion 25 is relatively large, the closing operation of the grip portion 24 is performed first and then the bending operation of the bending portion 25 is performed.

The operation resistance in a case where the grip portion 24 is closed includes friction at the intersecting portion of the pair of grip claws 30 and friction at a connecting portion between the grip claw 30 and the link member 31. Similarly, the operation resistance in a case where the bending portion 25 bends includes friction at a connecting portion between the two bending pieces 42 adjacent to each other. In addition, the outer coat 43 of the bending portion 25 is an elastic member that extends the bending portion 25 in a straight line, and the operation resistance in a case where the bending portion 25 bends includes elasticity of the outer coat 43. The operation wire 27 is also an elastic member that extends the bending portion 25 in a straight line, and the operation resistance in a case where the bending portion 25 bends includes elasticity of the operation wire 27. The elastic member that extends the bending portion 25 in a straight line is not limited to the outer coat 43 and the operation wire 27, and may be a wire spring or a leaf spring.

The bending portion 25 may be formed of a flexible pipe material made of an elastic material such as an elastomer, instead of the plurality of bending pieces 42 that are connected to be movable rotationally. In a case where the bending portion 25 is made of the flexible pipe material, the operation resistance in a case where the bending portion 25 bends includes elasticity of the pipe material.

Figure 10:
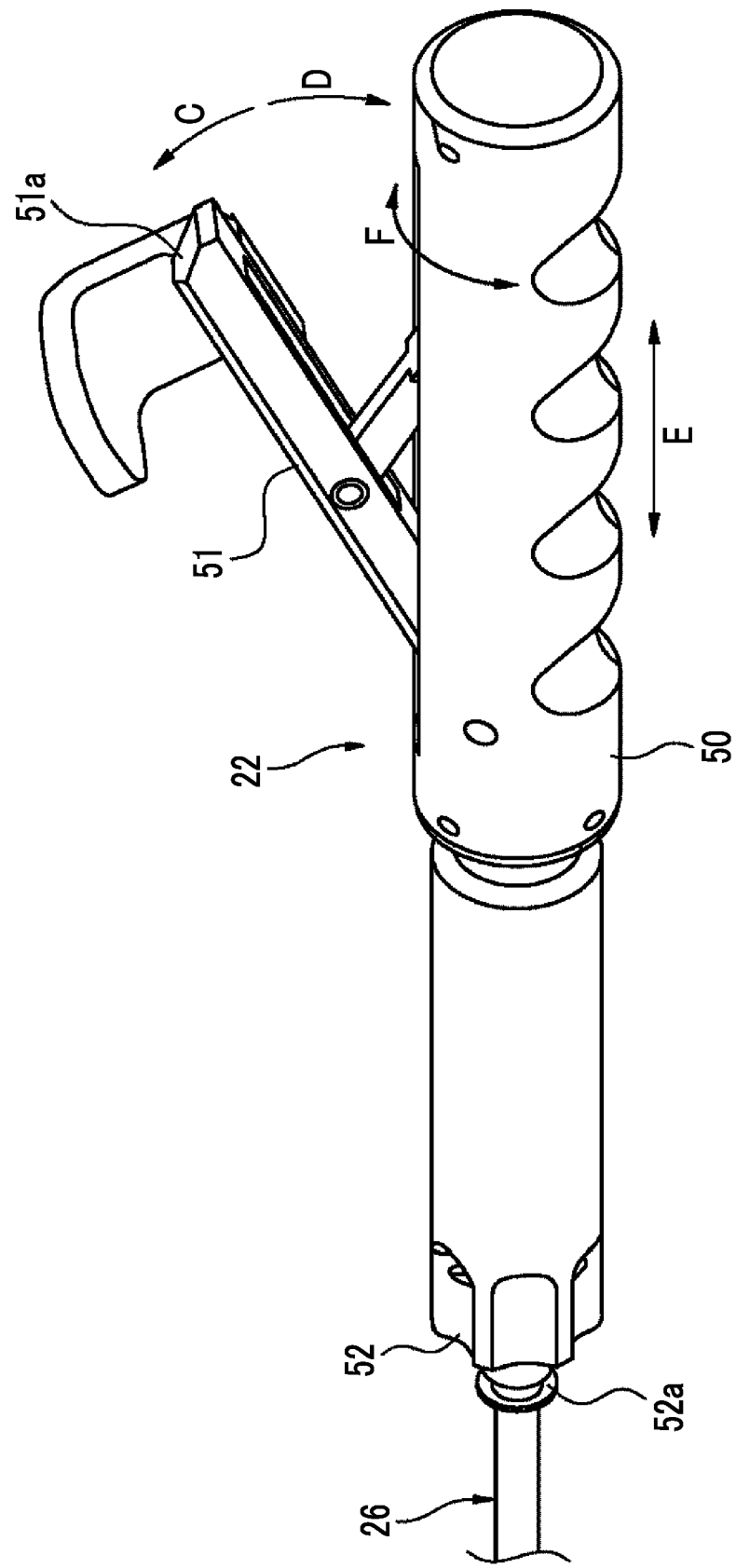
FIG. 10 is a view illustrating a configuration of an operation part of the endoscope treatment tool of FIG. 2.
Figure 11:
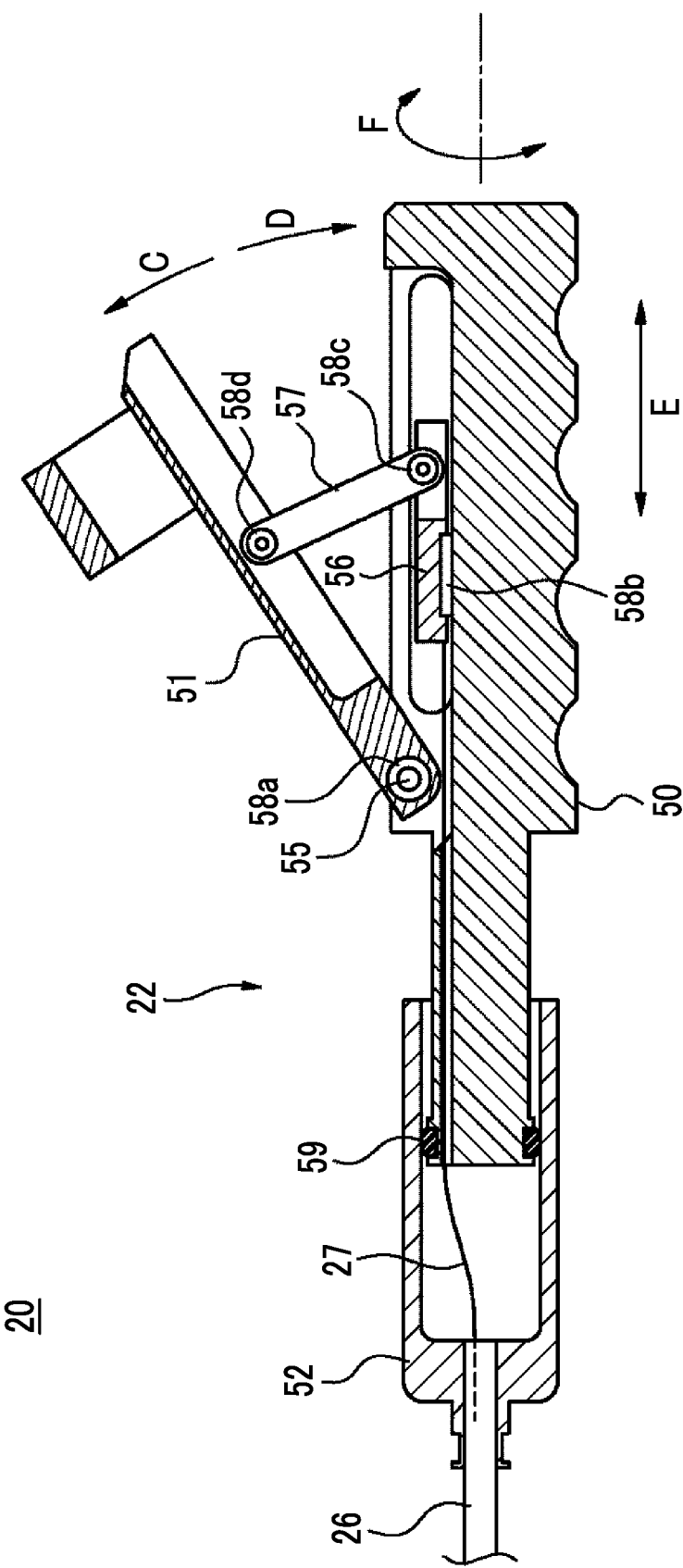
FIG. 11 is a cross-sectional view illustrating the operation part of the endoscope treatment tool of FIG. 2.

FIGS. 10 and 11 illustrate a configuration of the operation part 22.

The operation part 22 has an operation part body 50 that is an input unit for forward and backward movement/rotation operation of moving the grip portion 24 forward and backward and rotating the grip portion, an operation handle 51 that is an input unit for opening/closing/bending operation of opening and closing the grip portion 24 and bending the bending portion 25, and an attachment part 52 that is attachably and detachably attached to the endoscope operation part 7.

The attachment part 52 has a connection fitting 52a. The connection fitting 52a is connected to a base provided in the first treatment tool insertion opening 13 of the endoscope operation part 7. In a state where the connection fitting 52a is connected, the operation part 22 is supported by the endoscope operation part 7.

The operation part body 50 is formed in a rod shape, and is supported by the attachment part 52 so as to be operable in a central axis direction indicated with an arrow E and a rotation direction around a central axis indicated with an arrow F. The connecting portion 26 is connected to the operation part body 50 through the attachment part 52, and is moved forward and backward along a longitudinal axis of the connecting portion 26 in response to an operation of the operation part body 50 in an arrow E direction. In addition, the connecting portion 26 is rotated about the longitudinal axis of the connecting portion 26 in response to an operation of the operation part body 50 in an arrow F direction. The forward and backward movement and rotation of the connecting portion 26 are transmitted to the grip portion 24, and the grip portion 24 is also moved forward and backward and is rotated integrally with the connecting portion 26.

The operation handle 51 is swingably supported by the operation part body 50, and a free end portion 51a of the operation handle 51 is swingable in an opening direction C being spaced from the operation part body 50 and a closing direction D approaching the operation part body 50. The operation wire 27 is connected to the operation handle 51, and is pulled to the operation part 22 side and is pushed out to the distal end portion 23 side in response to an operation of the operation handle 51. Herein, with respect to the swing of the operation handle 51 in the opening direction C, the operation wire 27 may be pulled to the operation part 22 side or may be pushed out to the distal end portion 23 side. However, preferably, the operation wire 27 is pushed out to the distal end portion 23 side with respect to the swing of the operation handle 51 in the opening direction C, and the operation wire 27 is pulled to the operation part 22 side with respect to the swing in the closing direction D. In this case, as the operation handle 51 swings in the closing direction D, the grip portion 24 is closed and the bending portion 25 is bent.

The operation part 22 has a maintaining unit 58 that maintains an operation state of the operation handle 51, and is configured to be capable of maintaining a bending angle of the bending portion 25 at any angle that is equal to or smaller than a maximum bending angle.

The operation handle 51 is swingably supported by a shaft 55 fixed to the operation part body 50, and a friction member 58a, which is the maintaining unit 58, is attached thereto. The friction member 58a is made of, for example, rubber. The friction member 58a comes into sliding contact with a side surface of the operation handle 51, generates a frictional force with respect to the swing of the operation handle 51, and maintains the operation state of the operation handle 51 with the frictional force.

The maintaining unit 58 that maintains the operation state of the operation handle 51 may be a unit that generates a frictional force with respect to the swing of the operation handle 51, and is not limited to the friction member 58a attached to the shaft 55. For example, the operation part body 50 is provided with a slider 56, and the slider 56 is connected to the operation handle 51 via a link 57. In response to the swing of the operation handle 51, the link 57 rotates with respect to the operation handle 51 and the slider 56 as appropriate, and the slider 56 is moved along a central axis of the operation part body 50. The maintaining unit 58 that maintains the operation state of the operation handle 51 may be a friction member 58b which generates a frictional force through relative movement between the slider 56 and the operation part body 50, may be a friction member 58c that generates a frictional force through relative rotation between the slider 56 and the link 57, or may be a friction member 58d that generates frictional force through relative rotation between the link 57 and the operation handle 51. The friction members 58a to 58d may be used in a combination therewith as appropriate. In addition, the operation handle 51 may be fastened from the side surface to generate a frictional force.

In addition, the operation part 22 has a maintaining unit 59 that maintains the operation state of the operation part body 50 which is a forward and backward movement and rotation operation input unit. The attachment part 52 is formed in a tubular shape, the operation part body 50 is inserted inside the attachment part 52, and the maintaining unit 59 is attached to an outer peripheral surface of the operation part body 50. The maintaining unit 59 is made of, for example, rubber. The maintaining unit 59 comes into sliding contact with an inner peripheral surface of the attachment part 52, generates a frictional force with respect to the movement of the operation part body 50 in the arrow E direction and the rotation of the operation part body in the arrow F direction, and maintains the operation state of the operation part body 50 with a frictional force.

FIGS. 12 to 17 illustrate a treatment method for ESD as an example of a treatment method using the endoscope treatment tool 20. The operation wire 27 is pulled to the operation part 22 side with respect to the swing of the operation handle 51 in the closing direction D. In addition, an endoscope treatment tool used in combination with the endoscope treatment tool 20 is an incision tool, and is a high-frequency forcep 60 having a pair of openable and closable claws 61 at a distal end portion thereof (refer to FIG. 15). The pair of claws 61 are opened and closed by an operation part of the high-frequency forcep 60. In a state where the pair of claws 61 are closed and a living body tissue is gripped by the pair of claws 61, a high-frequency current flows between the pair of claws 61 and a return electrode plate via the living body tissue, or a high-frequency current flows between the pair of claws 61. Consequently, the living body tissue is cauterized and incision is performed.

The endoscope 2 is inserted into the body, and the endoscope distal end portion 10 is disposed on the side of a lesion part LA of a mucous membrane layer. The endoscope treatment tool 20 is inserted into the first treatment tool channel 14 of the endoscope 2, and the distal end portion 23 and the bending portion 25 of the endoscope treatment tool 20 protrude from the end surface of the endoscope distal end portion 10. Then, the lesion part LA is gripped by the grip portion 24 of the distal end portion 23 through operation of the operation part 22 of the endoscope treatment tool 20.

Figure 12:
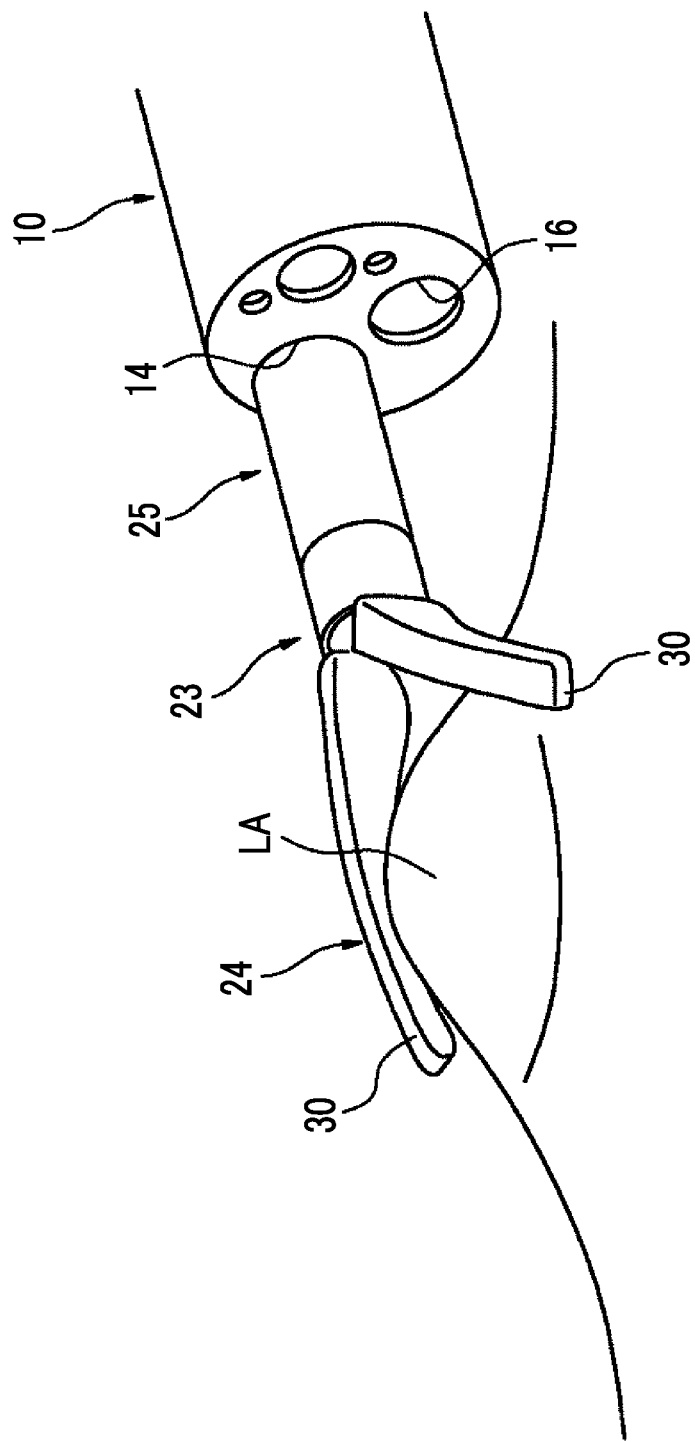
FIG. 12 is a view illustrating an example of a treatment method using the endoscope treatment tool of FIG. 2.

In a case where the lesion part LA is gripped by the grip portion 24, first, the operation handle 51 (refer to FIG. 10) of the operation part 22 is operated in the opening direction C. As illustrated in FIG. 12, as the operation wire 27 is pushed out to the distal end portion 23 side in response to the operation of the operation handle 51 and the operation wire 27 is pushed out, the bending portion 25 is extended in a straight line and is laid along the longitudinal axis of the connecting portion 26. In addition, as the operation wire 27 is pushed out, the pair of grip claws 30 of the grip portion 24 are opened. Then, the operation part body 50 is pushed and pulled as appropriate, and the lesion part LA is disposed between the pair of grip claws 30.

Figure 13:
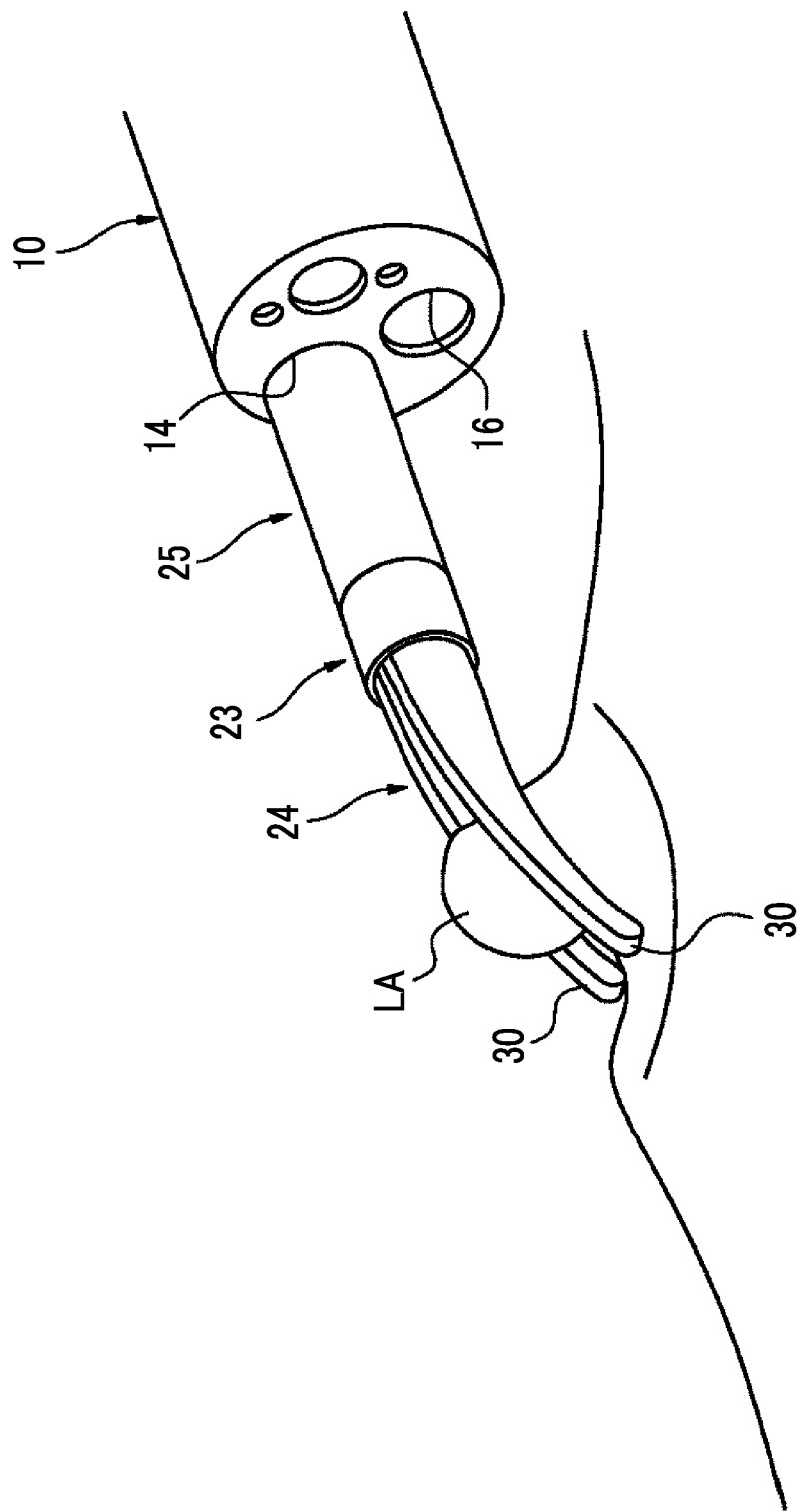
FIG. 13 is a view illustrating an example of the treatment method using the endoscope treatment tool of FIG. 2.
Figure 14:
FIG. 14 is a view illustrating an example of the treatment method using the endoscope treatment tool of FIG. 2.

The operation handle 51 is operated in the closing direction D in a state where the lesion part LA is disposed between the pair of grip claws 30. Accordingly, the operation wire 27 is pulled to the operation part 22 side. As the operation wire 27 is pulled, the pair of grip claws 30 are closed first and the lesion part LA is gripped by the grip portion 24 as illustrated in FIG. 13. Then, after the lesion part LA is gripped by the grip portion 24, the bending portion 25 is bent as illustrated in FIG. 14. Accordingly, the grip portion 24 is erected from a state of being laid along the longitudinal axis of the connecting portion 26, and the lesion part LA gripped by the grip portion 24 is lifted.

Figure 15:
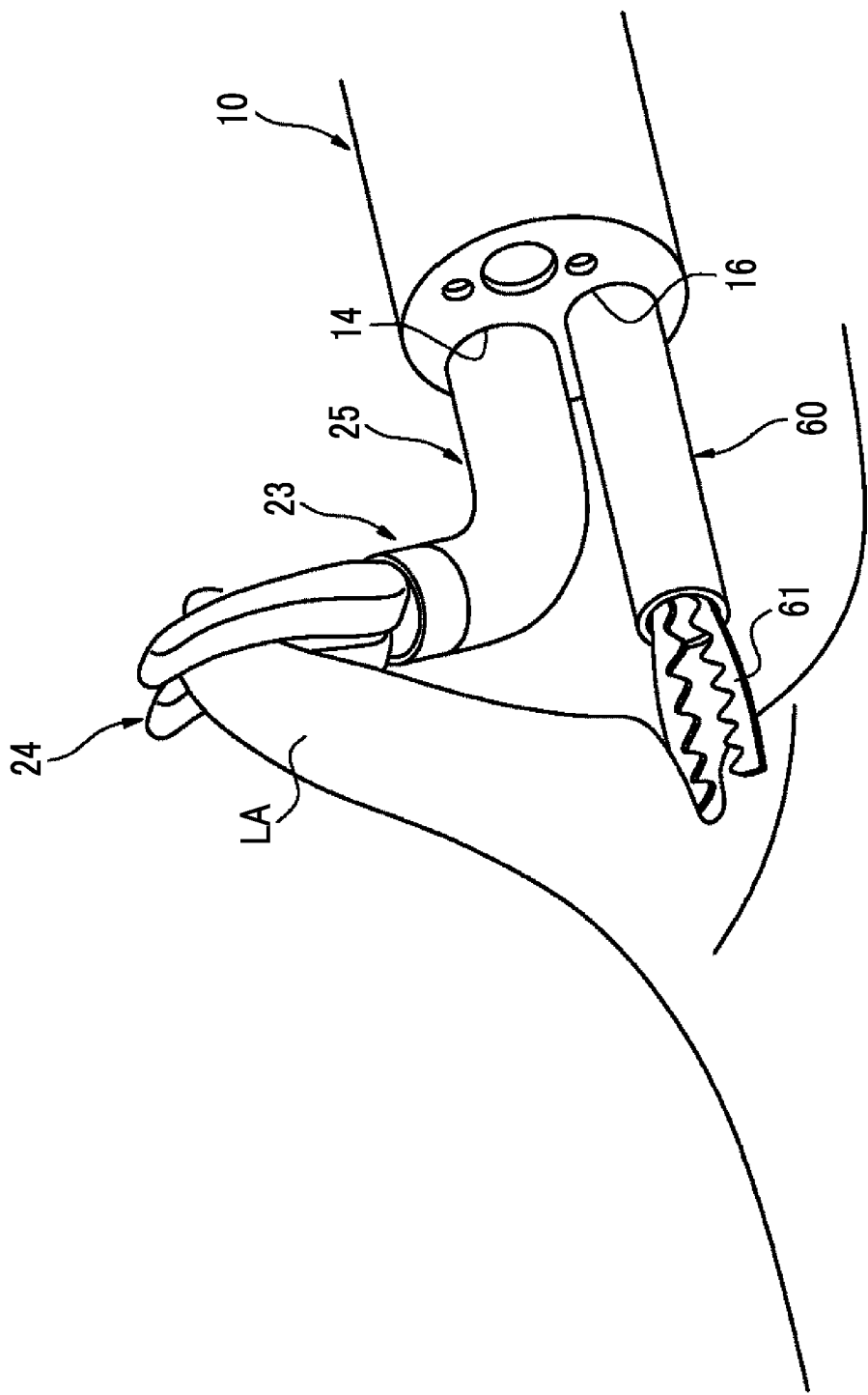
FIG. 15 is a view illustrating an example of the treatment method using a combination of the endoscope treatment tool of FIG. 2 and another endoscope treatment tool.

In a state where the lesion part LA is being lifted, the high-frequency forcep 60 inserted in the second treatment tool channel 16 of the endoscope 2 protrudes from the end surface of the endoscope distal end portion 10 as illustrated in FIG. 15. The pair of claws 61 of the high-frequency forcep 60 are disposed at a lower part of the lesion part LA, and the lower part of the lesion part LA is incised by the pair of claws 61. As the incision proceeds, the lifted lesion part LA may be released once, re-gripped, and then lifted. In a case where the lesion part LA that has been once incised is lifted, the lower part is exposed so that the lower part is easily visible. Therefore, excision can be performed safely, reliably, and easily. The incision proceeds as the high-frequency forcep 60 is pushed and pulled as appropriate, and the lesion part LA including a submucosal layer is gradually peeled off.

Since the lesion part LA can be gripped from the side of the lesion part LA and the gripped lesion part LA can be lifted only through operation of the operation handle 51 of the endoscope treatment tool 20 as described above, operation is simple. Accordingly, lifting of the lesion part LA, exposing the lower part of the lesion part LA so as to be easily visible by lifting the lesion part LA, and accordingly treatment for the lower part of the lifted lesion part LA can be performed safely, reliably, and easily. Further, in this example, the operation state of the operation handle 51 can be maintained by the maintaining unit 58. Therefore, even after the hand of an operator is separated from the operation handle 51, the lesion part LA can be kept at a lifted state. Accordingly, the operator can concentrate on the operation of the high-frequency forcep 60 in a case of incision, and by further simplifying the operation, the treatment for the lower part of the lesion part LA can be performed more easily.

In addition, in this example, the attachment part 52 of the endoscope treatment tool 20 is attachably and detachably attached to the endoscope operation part 7. In a state where the attachment part 52 is attached to the endoscope operation part 7, the operation part 22 of the endoscope treatment tool 20 can be supported by the endoscope operation part 7. Accordingly, by further simplifying the operation, treatment for the lower part of the lesion part LA can be performed more easily. Similar to the endoscope treatment tool 20, also the high-frequency forcep 60 may be attachably and detachably attached to the endoscope operation part 7.

In a case of incision, the operation part body 50 of the operation part 22 may be pushed and pulled in the arrow E direction of FIG. 10 and/or the operation part body 50 may be rotated in the arrow F direction of FIG. 10. As described above, the connecting portion 26 has stiffness that allows translational and rotational power to be transmitted from the operation part 22 side to the bending portion 25 side, and pushing, pulling, and rotation of the operation part body 50 are transmitted to the bending portion 25 via the connecting portion 26.

Figure 16:
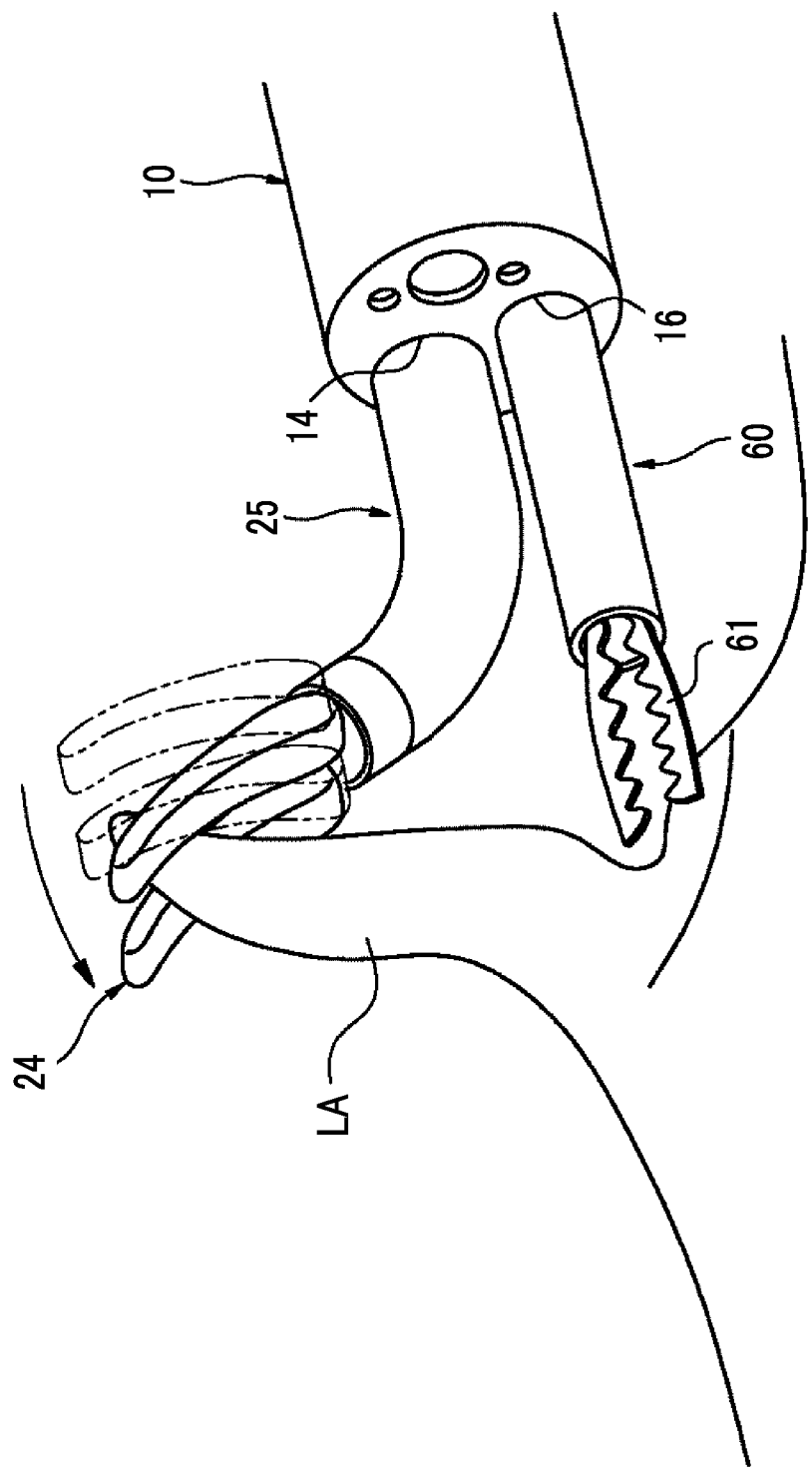
FIG. 16 is a view illustrating an example of a treatment method using a combination of the endoscope treatment tool of FIG. 2 and another endoscope treatment tool.

FIG. 16 illustrates a case where the operation part body 50 is rotated. The connecting portion 26 is rotated about the longitudinal axis of the connecting portion 26 in response to the rotation of the operation part body 50. In a state where the bending portion 25 is bent, the grip portion 24 is rotated while keeping an erected state with respect to the longitudinal axis of the connecting portion 26, and the lesion part LA gripped by the grip portion 24 swings about the longitudinal axis of the connecting portion 26.

Figure 17:
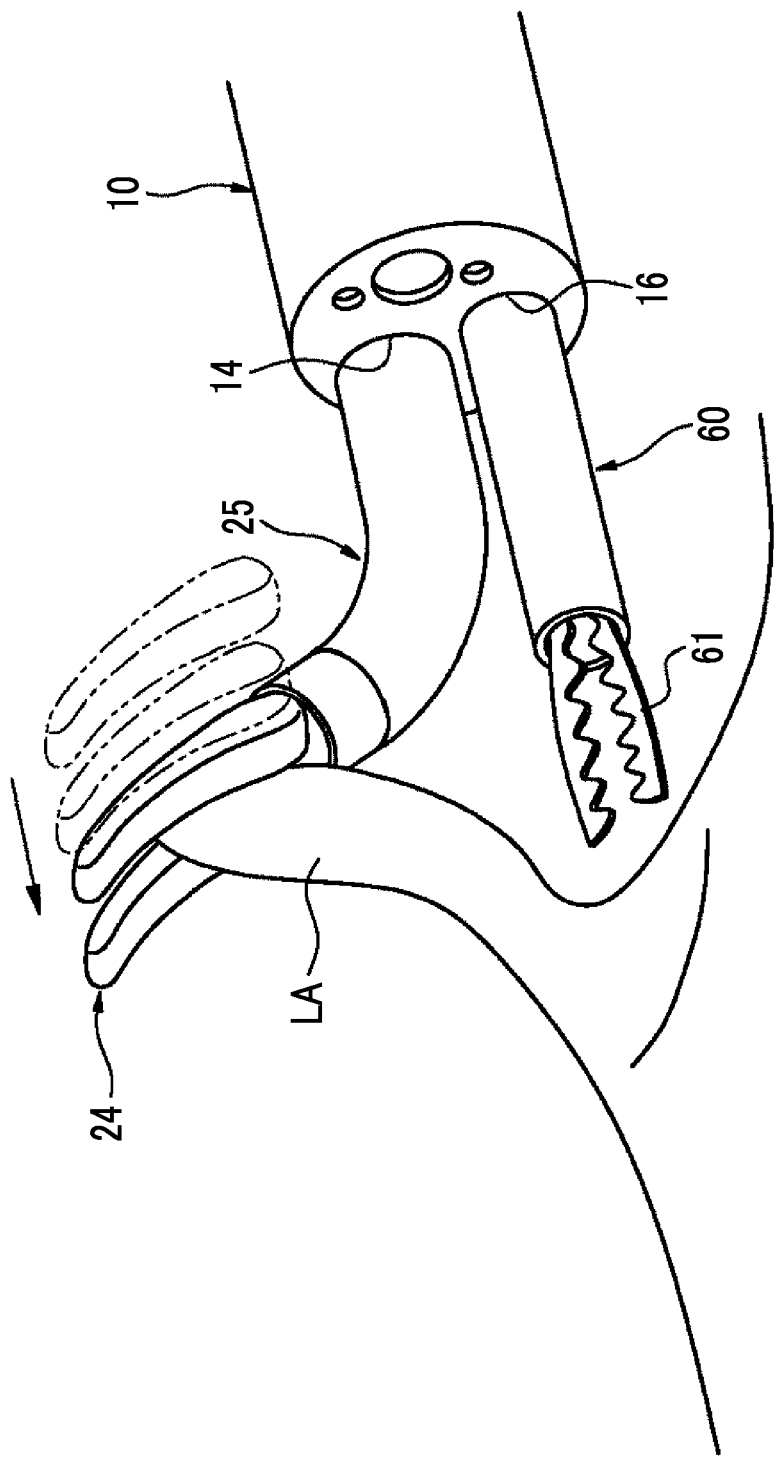
FIG. 17 is a view illustrating an example of a treatment method using a combination of the endoscope treatment tool of FIG. 2 and still another endoscope treatment tool.

FIG. 17 illustrates a case where the operation part body 50 is pushed and pulled. The connecting portion 26 is moved forward and backward in an axial direction of the longitudinal axis of the connecting portion 26 in response to the pushing and pulling of the operation part body 50. In a state where the bending portion 25 is bent, the grip portion 24 is moved forward and backward while keeping an erected state with respect to the longitudinal axis of the connecting portion 26, and the lesion part LA gripped by the grip portion 24 is pushed and pulled in the axial direction of the longitudinal axis of the connecting portion 26.

By swinging and/or pushing and pulling the lesion part LA as appropriate, for example, an incised wound can be widened. Accordingly, treatment for the lower part of the lesion part LA can be performed more easily. Thus, as the operation state of the operation part body 50 is maintained by the maintaining unit 59, the incised wound can be kept in a widened state even after the hand of the operator is separated from the operation part body 50. Accordingly, treatment for the lower part of the lesion part LA can be performed more easily.

In the endoscope treatment tool 20 described above, the operation part 22 may have a biasing member (not illustrated) such as a spring instead of the maintaining unit 58 that maintains the operation state of the operation handle 51, and the operation handle 51 may be biased by the biasing member in the closing direction D pulling the operation wire 27 to the operation part 22 side. Accordingly, even after the hand of the operator is separated from the operation handle 51, the grip portion 24 can be kept in a closed state and the bending portion 25 can be kept in a bent state.

Figure 18:
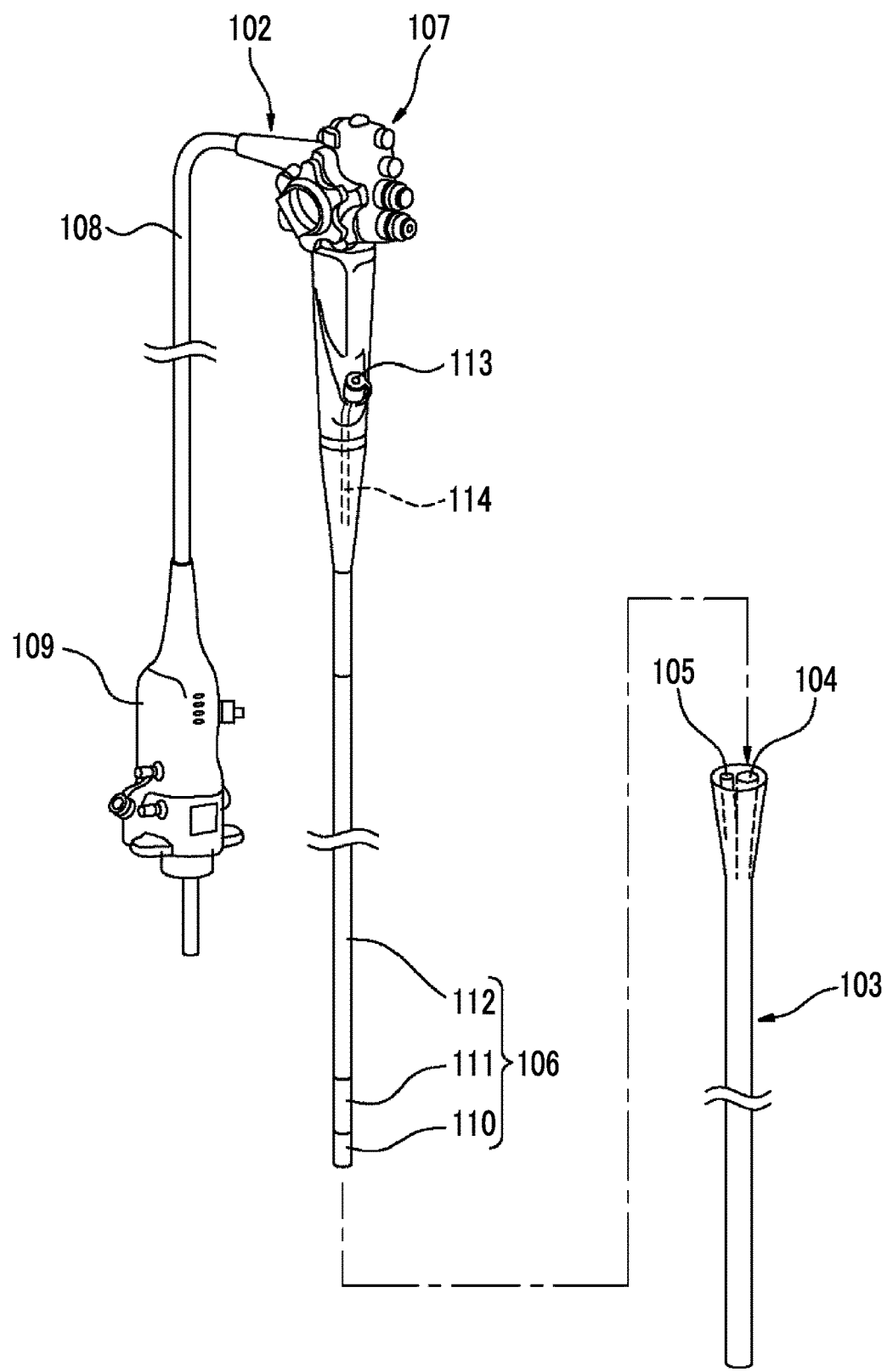
FIG. 18 is a view illustrating an example of the endoscope system, which is for describing the embodiment of the present invention.

FIG. 18 illustrates another example of the endoscope system, which is for describing the embodiment of the present invention.

An endoscope system 101 comprises an endoscope 102, a guide sheath 103, the light source device 3 (refer to FIG. 1), and the processor 4 (refer to FIG. 1). The endoscope 102 has an endoscope insertion part 106 that is inserted into a subject, an endoscope operation part 107 that is connected to the endoscope insertion part 106, and a universal cord 108 that extends from the endoscope operation part 107. The endoscope insertion part 106 is configured by an endoscope distal end portion 110, an endoscope bending portion 111 that is connected to the endoscope distal end portion 110, and an endoscope connecting portion 112 that connects the endoscope bending portion 111 to the endoscope operation part 107.

An image pick-up device including an imaging element is mounted on the endoscope distal end portion 110. The endoscope bending portion 111 is configured to be able to be bent, and the bending of the endoscope bending portion 111 is operated by the endoscope operation part 107. In addition, the endoscope connecting portion 112 is configured to be flexible so as to be deformable along a shape of an insertion passage in the subject.

The endoscope operation part 107 is provided with an operation button for operating image pick-up using the image pick-up device and an operation knob for operating the bending of the endoscope bending portion 111. In addition, the endoscope operation part 107 is provided with a treatment tool insertion opening 113 into which the endoscope treatment tool is insertable. Inside the endoscope insertion part 106, a treatment tool channel 114 that reaches the endoscope distal end portion 110 from the treatment tool insertion opening 113 and is open to an end surface of the endoscope distal end portion 110 is provided.

A light guide and a cable are provided inside the endoscope insertion part 106, the endoscope operation part 107, and the universal cord 108. A connector 109 is provided at a terminal of the universal cord 108. The endoscope 102 is connected to the light source device 3 and the processor 4 via the connector 109.

The guide sheath 103 is configured to be flexible so as to be deformable along a shape of an insertion passage in the subject, and has an endoscope channel 104 into which the endoscope insertion part 106 is insertable and a treatment tool channel 105 into which the endoscope treatment tool is insertable. The endoscope channel 104 and the treatment tool channel 105 extend over the entire length of the guide sheath 103.

In the endoscope system 101, the endoscope treatment tool 20 illustrated from FIGS. 2 to 11 is used by being inserted into one of the treatment tool channel 114 of the endoscope 102 or the treatment tool channel 105 of the guide sheath 103, and another endoscope treatment tool that is used in combination with the endoscope treatment tool 20 is inserted into the other one of the treatment tool channel 114 or the treatment tool channel 105.

FIGS. 19 to 22 illustrate a treatment method for ESD as an example of the treatment method using the endoscope treatment tool 20. The endoscope treatment tool 20 is inserted into the treatment tool channel 105 of the guide sheath 103. In addition, a second endoscope treatment tool used in combination with the endoscope treatment tool 20 is the high-frequency forcep 60 illustrated in FIG. 15.

First, the guide sheath 103 is inserted into the body. Next, the endoscope insertion part 106 is inserted into the endoscope channel 104 of the guide sheath 103, and the endoscope distal end portion 110 protruding from a distal end surface of the guide sheath 103 is disposed at the side of the lesion part LA of a mucous membrane layer. Next, the endoscope treatment tool 20 is inserted into the treatment tool channel 105 of the guide sheath 103, and the distal end portion 23 and the bending portion 25 of the endoscope treatment tool 20 protrude from the distal end surface of the guide sheath 103. Then, the lesion part LA is gripped by the grip portion 24 of the distal end portion 23 through operation of the operation part 22 of the endoscope treatment tool 20.

Figure 19:
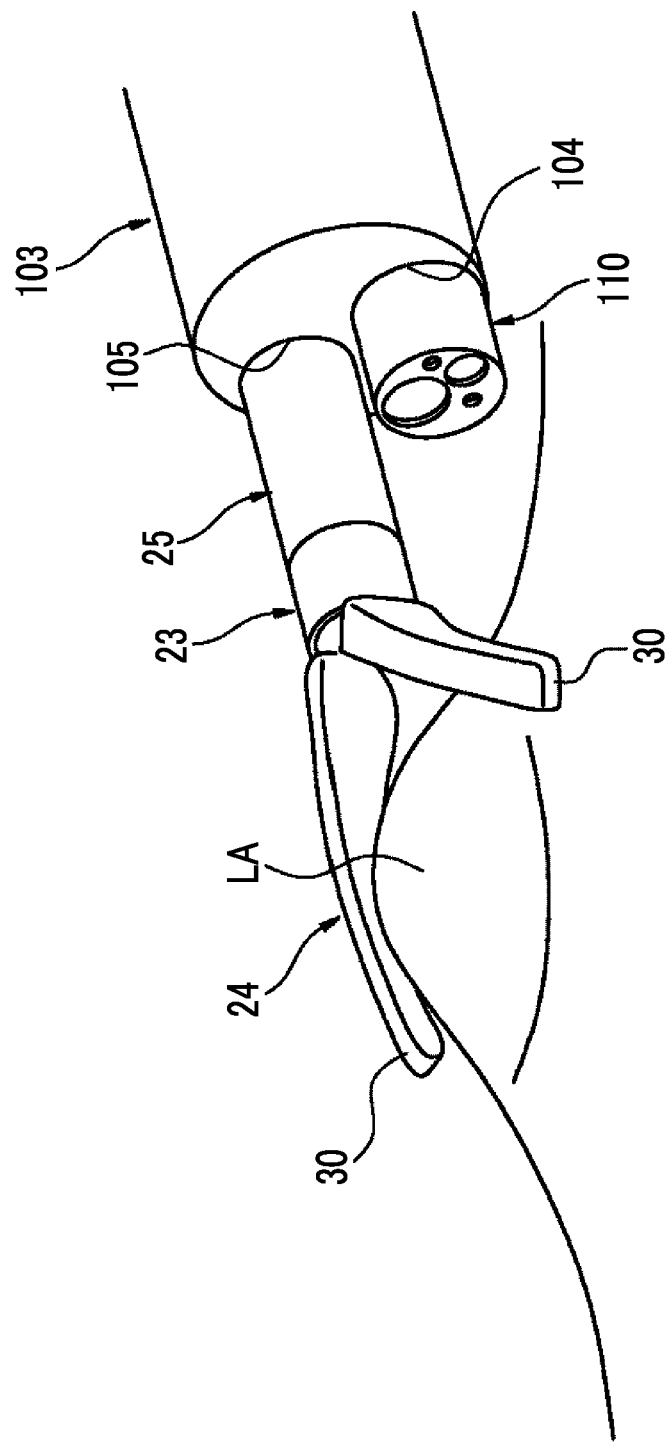
FIG. 19 is a view illustrating an example of the treatment method using the endoscope treatment tool of FIG. 2.

In a case where the lesion part LA is gripped by the grip portion 24, first, the operation handle 51 (refer to FIG. 10) of the operation part 22 is operated in the opening direction C. As illustrated in FIG. 19, the operation wire 27 is pushed out to the distal end portion 23 side in response to the operation of the operation handle 51. As the operation wire 27 is pushed out, the bending portion 25 is extended in a straight line and is laid along the longitudinal axis of the connecting portion 26. In addition, as the operation wire 27 is pushed out, the pair of grip claws 30 of the grip portion 24 are opened. Then, the operation part body 50 is pushed and pulled as appropriate, and the lesion part LA is disposed between the pair of grip claws 30.

Figure 20:
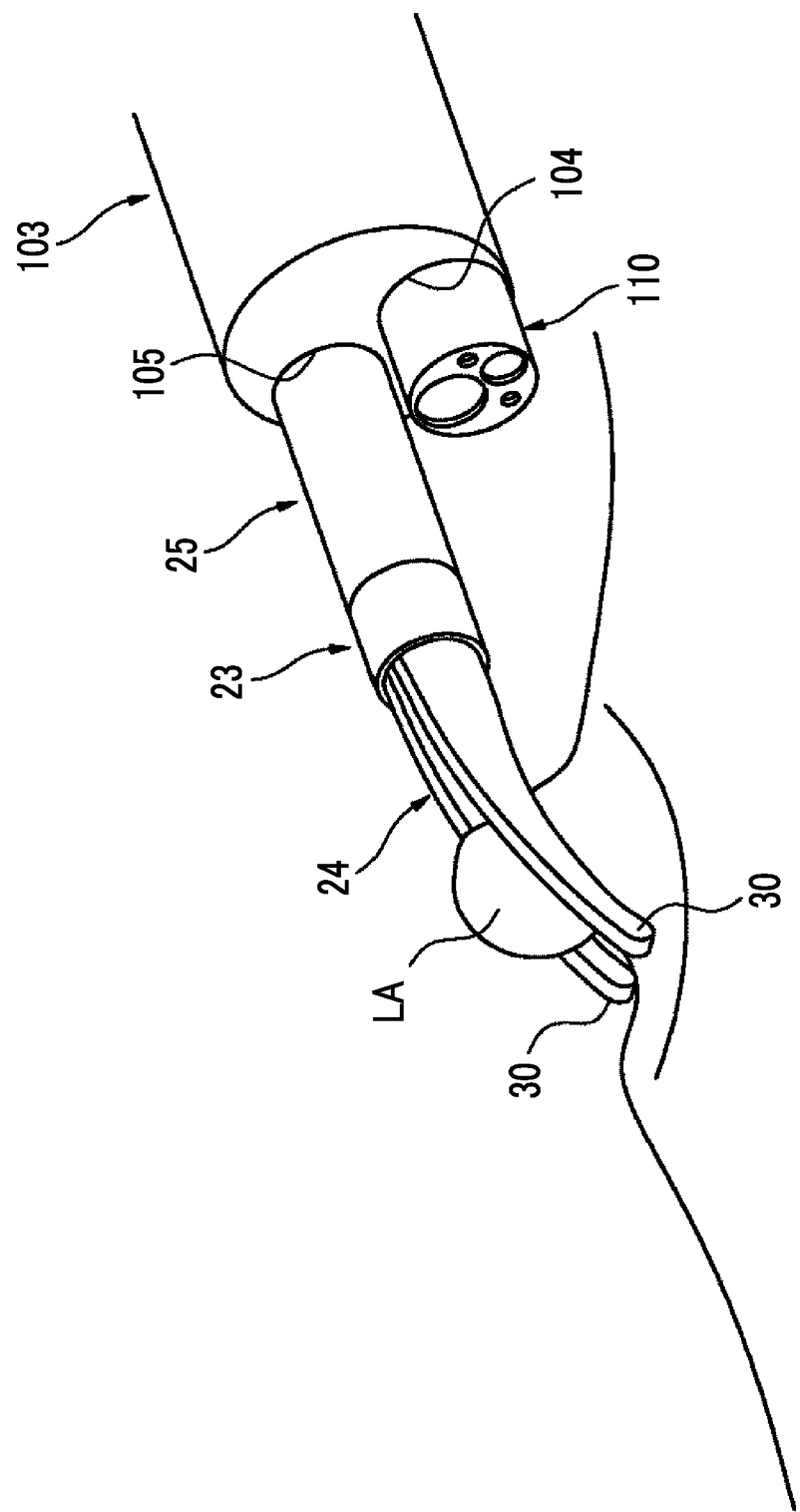
FIG. 20 is a view illustrating an example of the treatment method using the endoscope treatment tool of FIG. 2.
Figure 21:
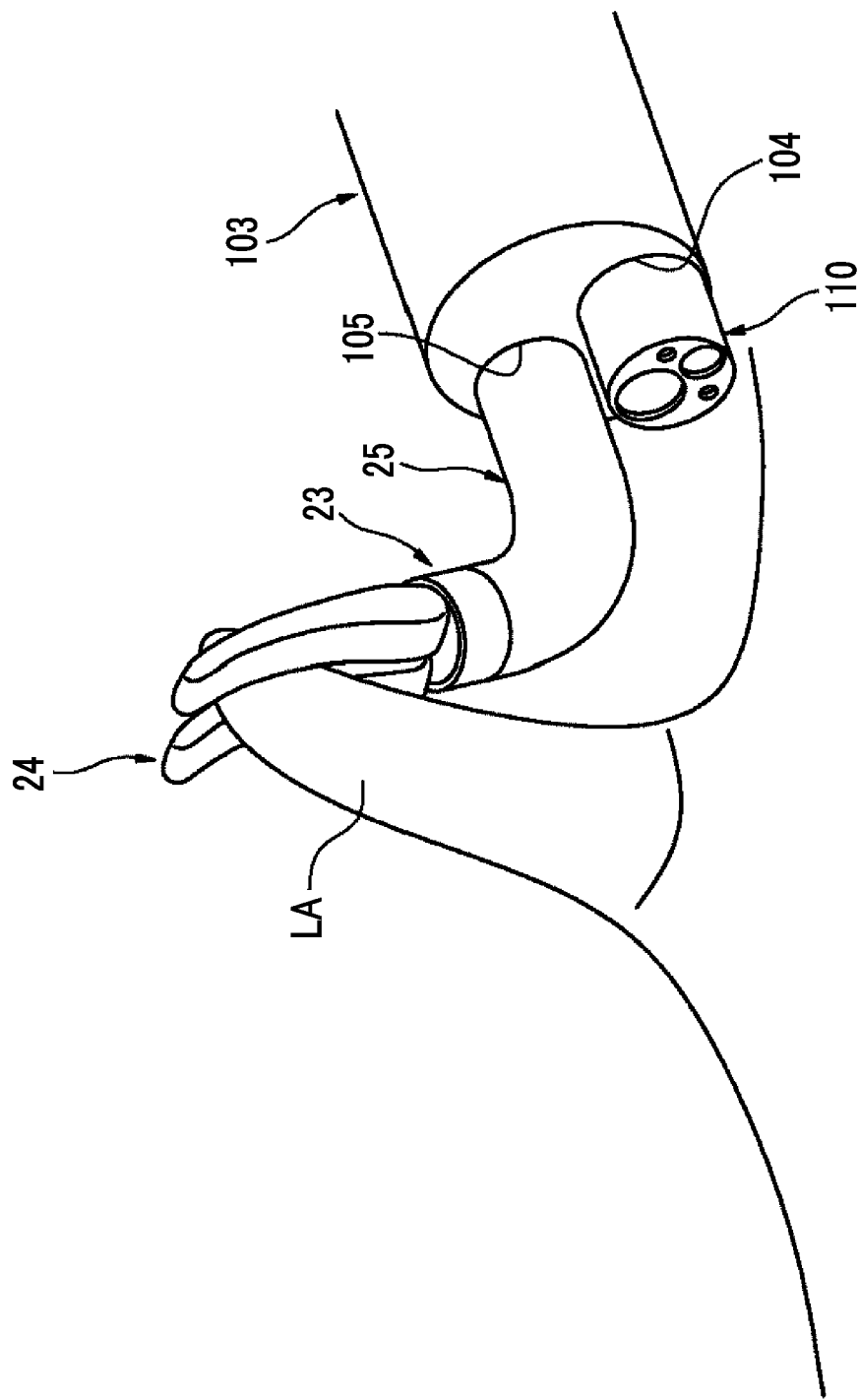
FIG. 21 is a view illustrating an example of the treatment method using the endoscope treatment tool of FIG. 2.

The operation handle 51 is operated in the closing direction D in a state where the lesion part LA is disposed between the pair of grip claws 30. Accordingly, the operation wire 27 is pulled to the operation part 22 side. As the operation wire 27 is pulled, the pair of grip claws 30 are closed first and the lesion part LA is gripped by the grip portion 24 as illustrated in FIG. 20. Then, after the lesion part LA is gripped by the grip portion 24, the bending portion 25 is bent as illustrated in FIG. 21. Accordingly, the grip portion 24 is erected from a state of being laid along the longitudinal axis of the connecting portion 26, and the lesion part LA gripped by the grip portion 24 is lifted.

Figure 22:
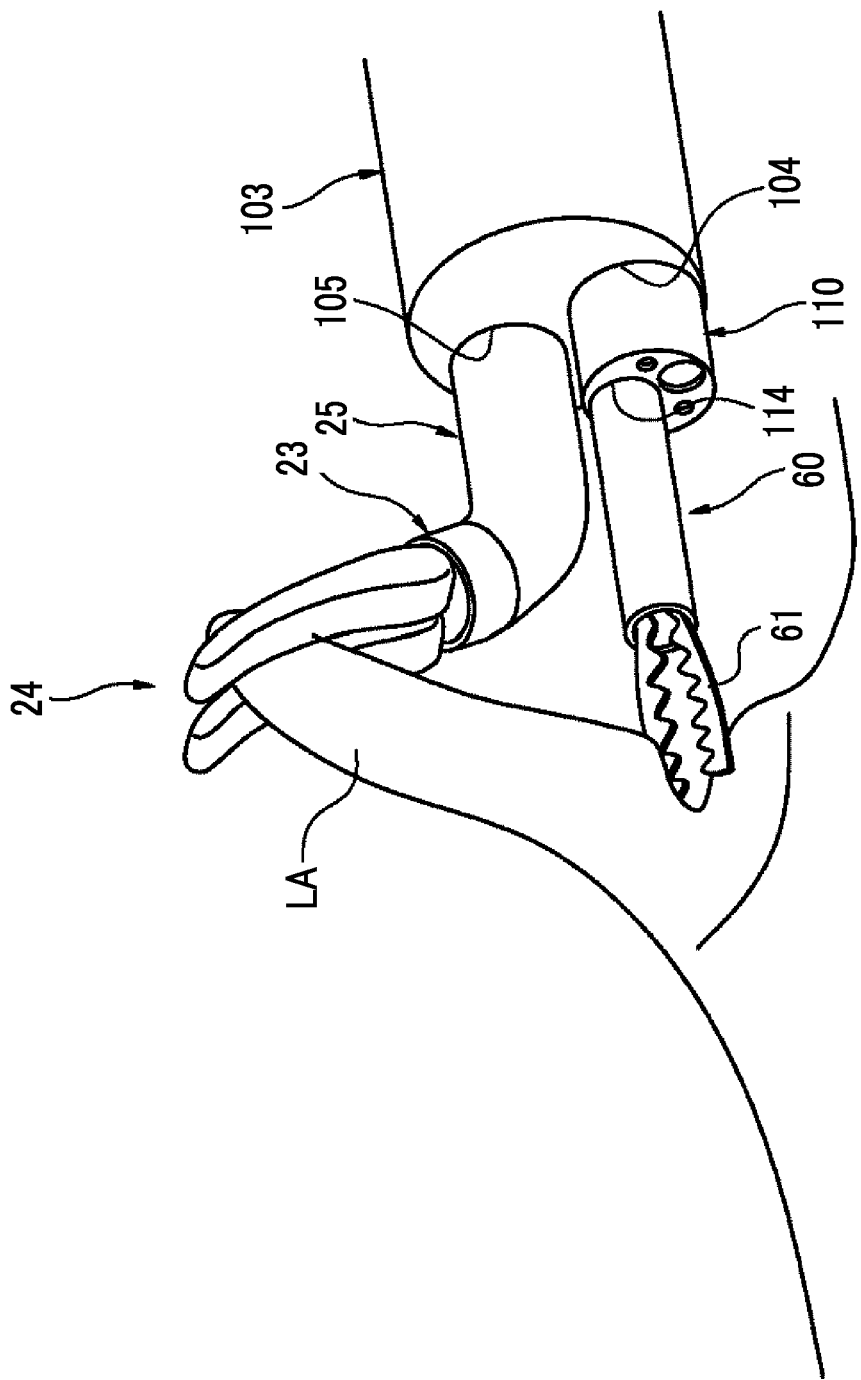
FIG. 22 is a view illustrating an example of the treatment method using a combination of the endoscope treatment tool of FIG. 2 and another endoscope treatment tool.

In a state where the lesion part LA is being lifted, the high-frequency forcep 60 inserted in the treatment tool channel 114 of the endoscope 102 protrudes from the end surface of the endoscope distal end portion 110 as illustrated in FIG. 22. The pair of claws 61 of the high-frequency forcep 60 are disposed at the lower part of the lesion part LA, and the lower part of the lesion part LA is incised by the pair of claws 61.

In a case of incision, the operation part body 50 of the operation part 22 may be pushed and pulled in the arrow E direction of FIG. 10 and/or the operation part body 50 may be rotated in the arrow F direction of FIG. 10. The lesion part LA gripped by the grip portion 24 is pushed and pulled in the axial direction of the longitudinal axis of the connecting portion 26 in response to the pushing and pulling of the operation part body 50, and the lesion part LA gripped by the grip portion 24 swings about the longitudinal axis of the connecting portion 26 in response to the rotation of the operation part body 50. By swinging and/or pushing and pulling the lesion part LA as appropriate, for example, an incised wound can be widened. Accordingly, treatment for the lower part of the lesion part LA can be performed more easily.

Since the lesion part LA can be gripped from the side of the lesion part LA and the gripped lesion part LA can be lifted only through operation of the operation handle 51 of the endoscope treatment tool 20 as described above, operation is simple. Accordingly, lifting of the lesion part LA, exposing the lower part of the lesion part LA so as to be easily visible by lifting the lesion part LA, and accordingly treatment for the lower part of the lifted lesion part LA can be performed safely, reliably, and easily.

Although the endoscope treatment tool 20 has been described as being inserted into the treatment tool channel 105 of the guide sheath 103, the endoscope treatment tool 20 may be inserted into the treatment tool channel 114 of the endoscope 102, and the high-frequency forcep 60 may be inserted into the treatment tool channel 105 of the guide sheath 103.

Figure 23:
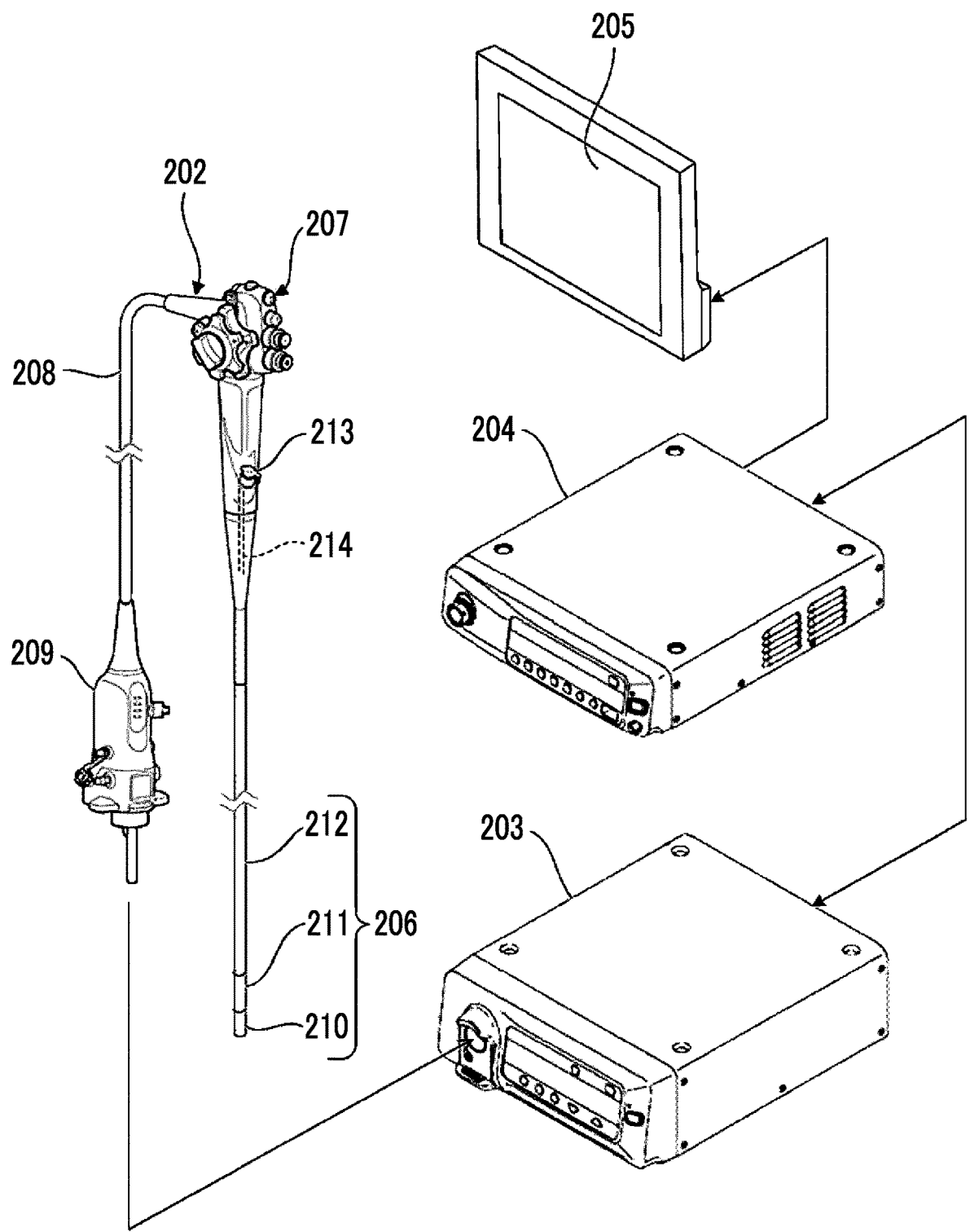
FIG. 23 is a view illustrating an example of an endoscope system, which is for describing the embodiment of the present invention.

FIG. 23 illustrates an example of an endoscope system, which is for describing the embodiment of the present invention.

An endoscope system 201 comprises an endoscope 202, a light source device 203, and a processor 204. The endoscope 202 has an endoscope insertion part 206 that is inserted into a subject, an endoscope operation part 207 that is connected to the endoscope insertion part 206, and a universal cord 208 that extends from the endoscope operation part 207. The endoscope insertion part 206 is configured by an endoscope distal end portion 210, an endoscope bending portion 211 that is connected to the endoscope distal end portion 210, and an endoscope connecting portion 212 that connects the endoscope bending portion 211 to the endoscope operation part 207.

An image pick-up device including an imaging element is mounted on the endoscope distal end portion 210. The endoscope bending portion 211 is configured to be able to be bent, and the bending of the endoscope bending portion 211 is operated by the endoscope operation part 207. In addition, the endoscope connecting portion 212 is configured to be flexible so as to be deformable along a shape of an insertion passage in the subject.

The endoscope operation part 207 is provided with an operation button for operating image pick-up using the image pick-up device and an operation knob for operating the bending of the endoscope bending portion 211. In addition, the endoscope operation part 207 is provided with a treatment tool insertion opening 213 into which the endoscope treatment tool is insertable. Inside the endoscope insertion part 206, a treatment tool channel 214 that reaches the endoscope distal end portion 210 from the treatment tool insertion opening 213 and is open to an end surface of the endoscope distal end portion 210 is provided.

A light guide and a cable are provided inside the endoscope insertion part 206, the endoscope operation part 207, and the universal cord 208. A connector 209 is provided at a terminal of the universal cord 208. The endoscope 202 is connected to the light source device 203 and the processor 204 via the connector 209.

Illumination light generated by the light source device 203 is guided to the endoscope distal end portion 210 via the light guide and is emitted from the endoscope distal end portion 210. In addition, operating power of the imaging element, a control signal for driving the imaging element, and an image signal output from the imaging element are transmitted between the processor 204 and the image pick-up device via the cable. The processor 204 processes the input image signal to generate image data of an observed part in the subject, displays the generated image data on a monitor 205, and records the generated image data.

Figure 24:
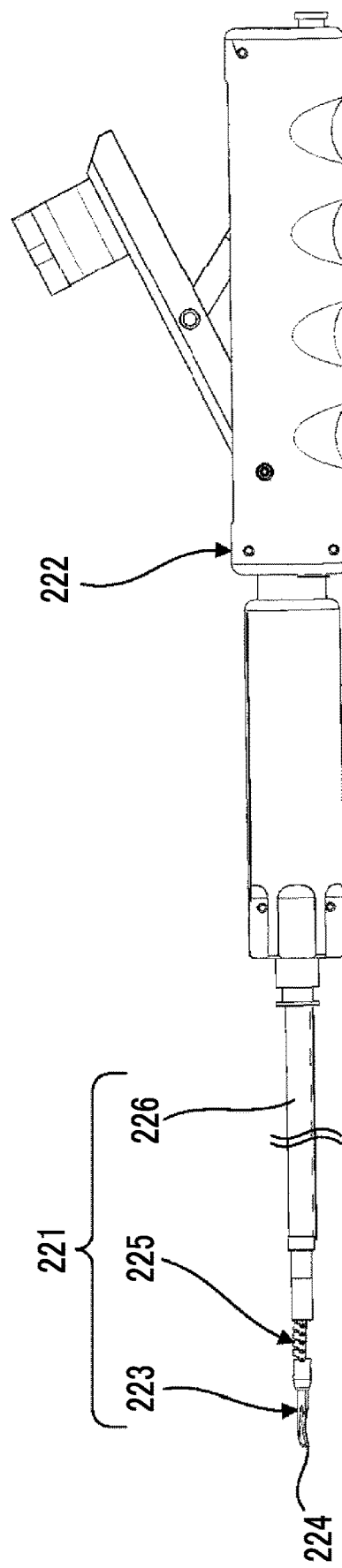
FIG. 24 is a view illustrating an example of an endoscope treatment tool, which is for describing the embodiment of the present invention.

FIG. 24 illustrates an example of the endoscope treatment tool, which is for describing the embodiment of the present invention.

An endoscope treatment tool 220 comprises an insertion part 221 that is insertable into the treatment tool channel 214 (refer to FIG. 23) and an operation part 222. The insertion part 221 includes a distal end portion 223 that has a grip portion 224 which is operated to be opened and closed by the operation part 222, a bending portion 225 that is provided to be adjacent to an operation part side of the distal end portion 223, and a connecting portion 226 that connects the bending portion 225 to the operation part 222.

In a case where the insertion part 221 is inserted in the treatment tool channel 214, the distal end portion 223 and the bending portion 225 protrude from the end surface of the endoscope distal end portion 210 (refer to FIG. 23), and the connecting portion 226 is accommodated in the treatment tool channel 214. Similar to the endoscope connecting portion 212, the connecting portion 226 accommodated in the treatment tool channel 214 is configured to be flexible so as to be deformable along the shape of the insertion passage in the subject.

Figure 25:
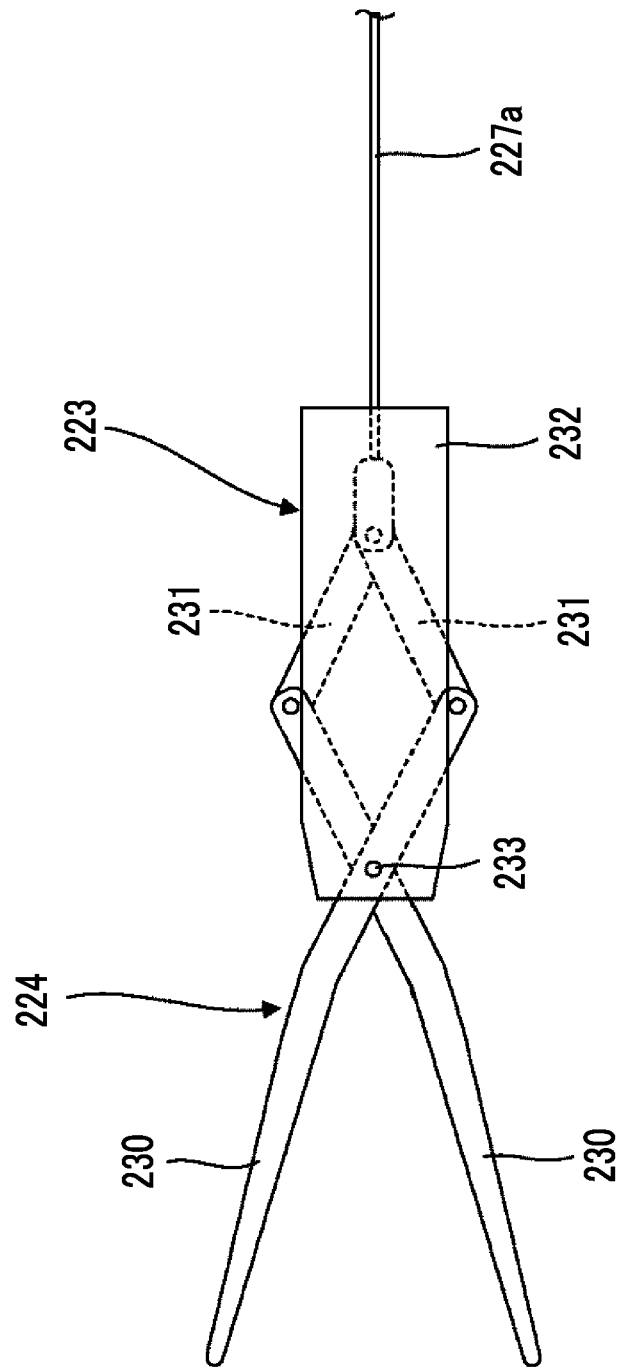
FIG. 25 is a view illustrating a configuration of a grip portion of a distal end portion of the endoscope treatment tool of FIG. 24.
Figure 26:
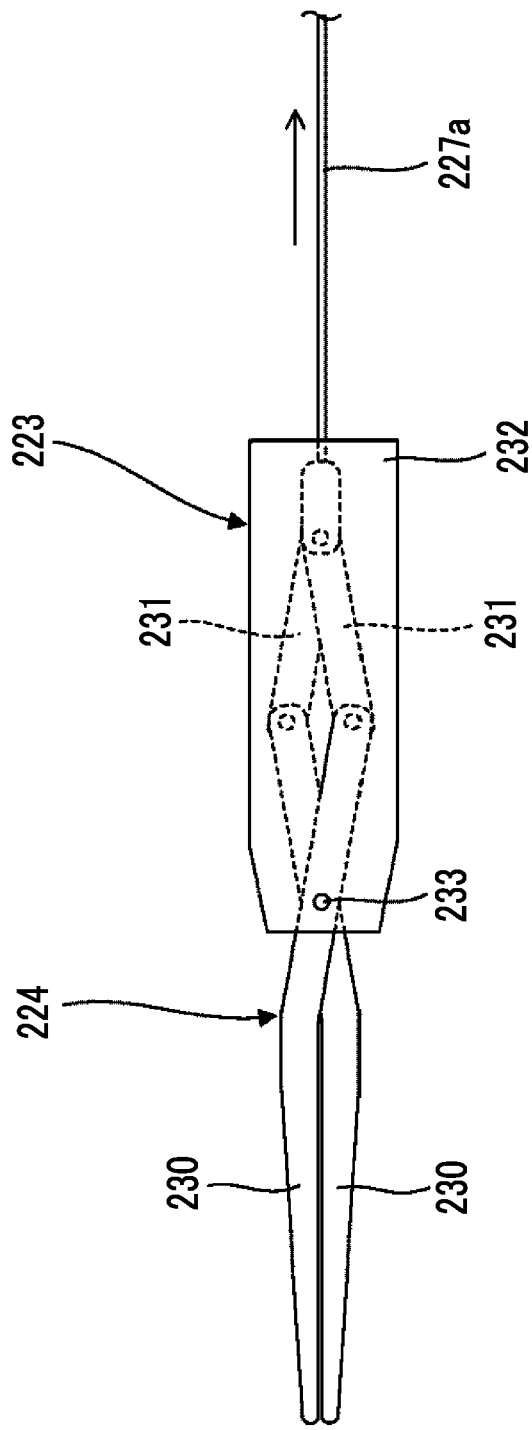
FIG. 26 is a view illustrating an operation of the grip portion of FIG. 25.

FIGS. 25 and 26 illustrate a configuration and an operation of the grip portion 224 of the distal end portion 223.

In the example illustrated in FIG. 25, the grip portion 224 has a pair of grip claws 230 and a pair of link members 231, and the distal end portion 223 has a support body 232 that supports the pair of grip claws 230 so as to be movable rotationally. The pair of grip claws 230 are disposed to intersect each other, and a pin 233 is provided to penetrate an intersecting portion of the pair of grip claws 230. The pin 233 is fixed to the support body 232, and the grip claws 230 are supported by the support body 232 so as to be movable rotationally about the pin 233 which is a rotation axis.

Distal end portions of the link members 231 are connected to proximal end portions of the grip claws 230 so as to be movable rotationally, and an operation wire 227a is connected to proximal end portions of the link members 231. The operation wire 227a reaches the operation part 222 from the distal end portion 223 via the bending portion 225 and the connecting portion 226, and is pulled to an operation part 222 side or is pushed out to a distal end portion 223 side in response to operation of the operation part 222.

FIG. 25 illustrates a state where the operation wire 227a is pushed out to the distal end portion 223 side, and distal end portions of the pair of grip claws 230 are open. As the operation wire 227a is pulled to the operation part 222 side, the distal end portions of the pair of grip claws 230 are closed as illustrated in FIG. 26. A part to be treated of a living body is gripped by the distal end portions of the pair of closed grip claws 230.

Figure 27:
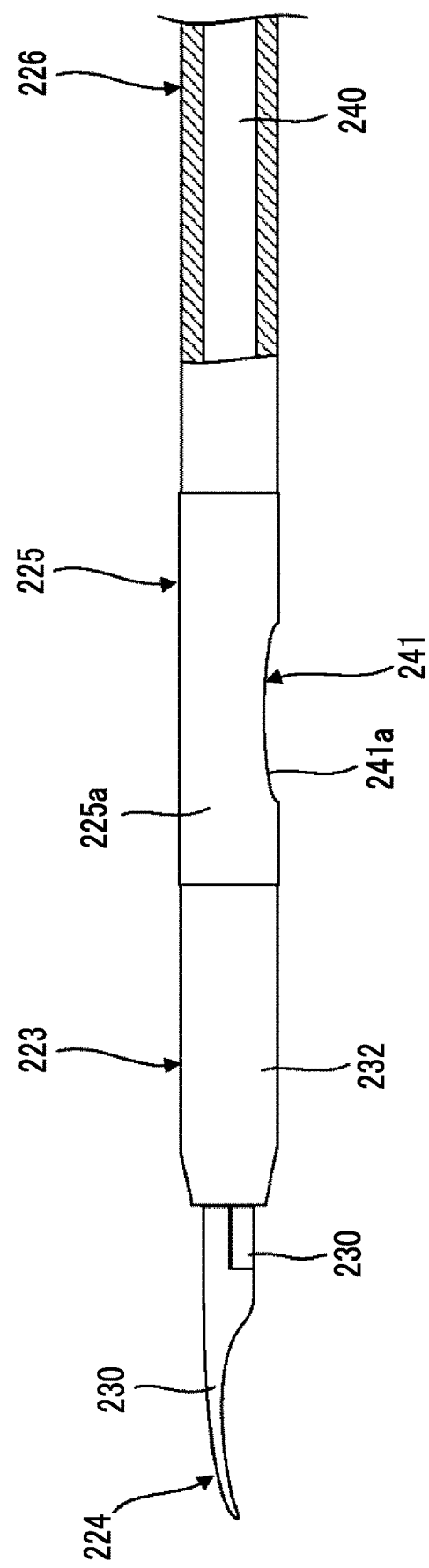
FIG. 27 is a view illustrating configurations of a bending portion and a connecting portion of the endoscope treatment tool of FIG. 24.
Figure 28:
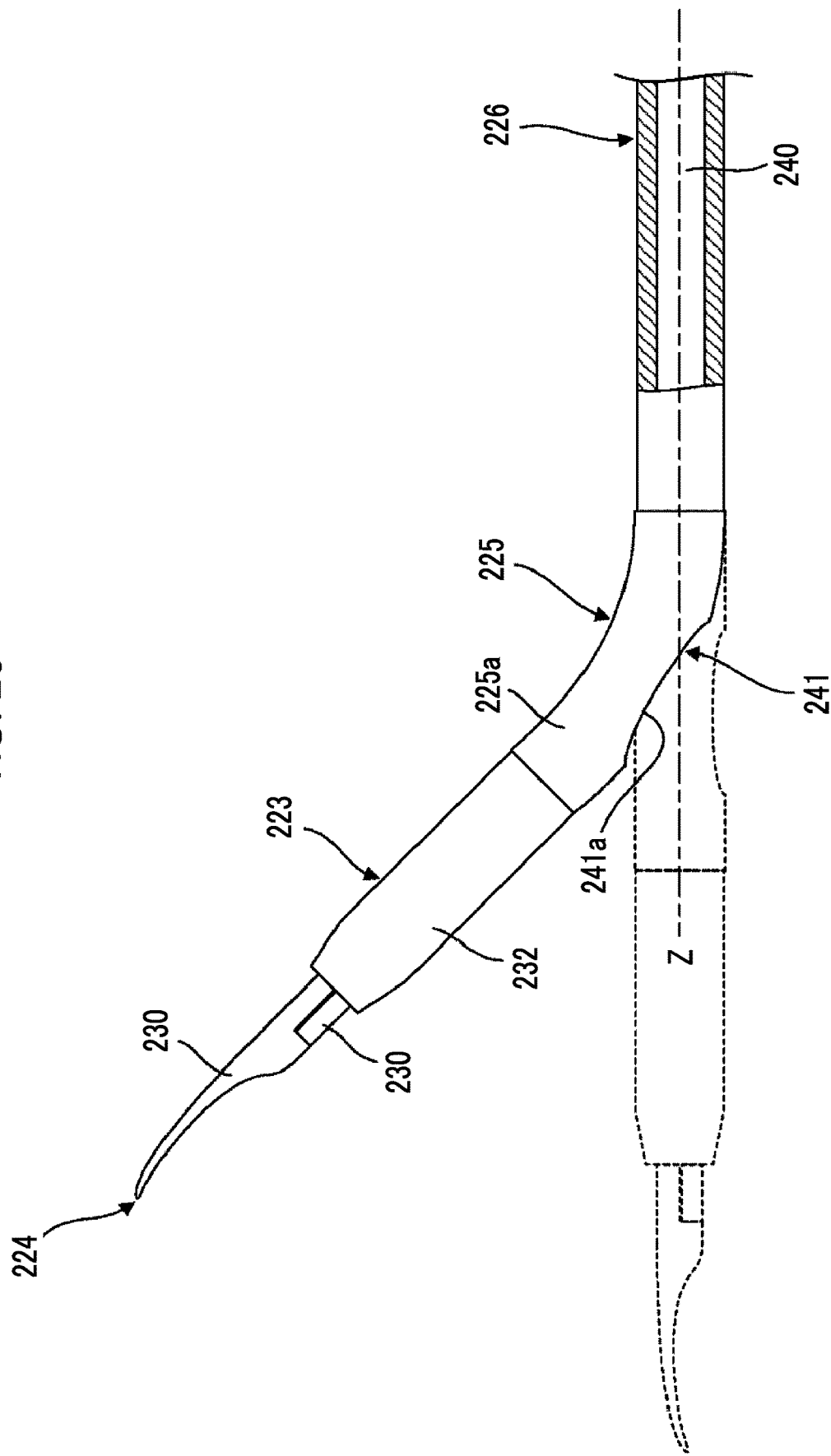
FIG. 28 is a view illustrating an operation of the bending portion of FIG. 27.

FIGS. 27 and 28 illustrate configurations and operations of the bending portion 225 and the connecting portion 226.

The connecting portion 226 has flexibility and also has stiffness that allows translational and rotational power to be transmitted from the operation part 222 side to a bending portion 225 side. Such a connecting portion 226 can be configured, for example, such that an outer periphery of a screw pipe, which is formed by spirally winding a metal strip plate material, is covered with a mesh pipe formed by braiding a metal wire and an outer periphery of the mesh pipe is covered with a resin outer coat.

The connecting portion 226 has a pipe line 240, into which another endoscope treatment tool is insertable, therein. In the configuration, the inside of a screw pipe is the pipe line 240. Examples of another endoscope treatment tool include an incision tool such as a high-frequency knife (a cylindrical type, a distal end insulation type, and a scissors type) that incises a part to be treated of a living body, an injection needle that injects a drug solution into the part to be treated, a suction needle that collects a tissue of the part to be treated, a clip for hemostasis, a collection net, and a bending treatment tool.

The bending portion 225 has a pipe line outlet 241 that communicates with the pipe line 240 and is open to an outer peripheral surface 225a of the bending portion 225. As illustrated in FIG. 28, the bending portion 225 is able to be bent in a curve shape in which the pipe line outlet 241 is disposed outside the curve (hereinafter, referred to as a predetermined curve shape) and is operated to be bent by the operation part 222. In a case where the bending portion 225 is operated to be bent into the predetermined curve shape, an opening 241a of the pipe line outlet 241 in the outer peripheral surface 225a is disposed to intersect a pipe axis Z of the pipe line 240.

Figure 29:
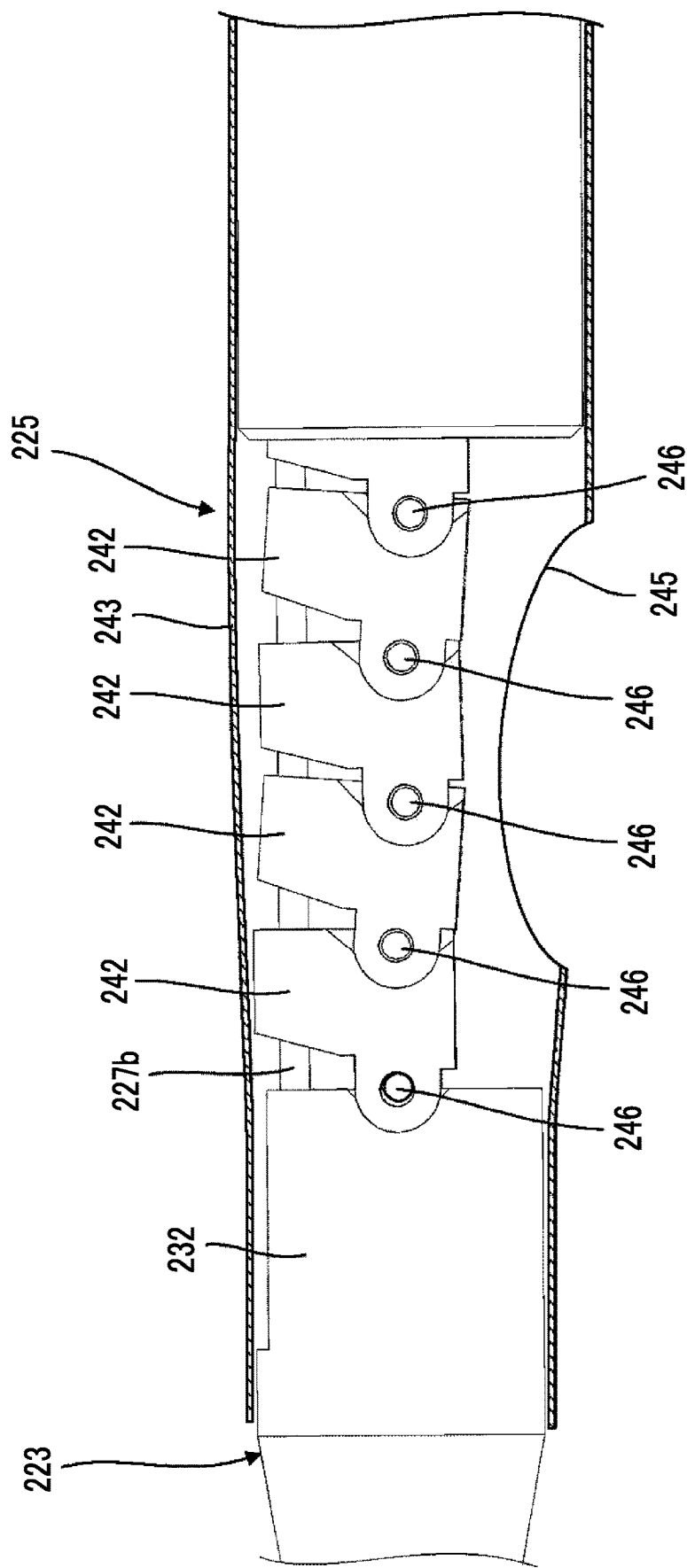
FIG. 29 is a view illustrating a configuration of an inside of the bending portion of FIG. 27.
Figure 30:
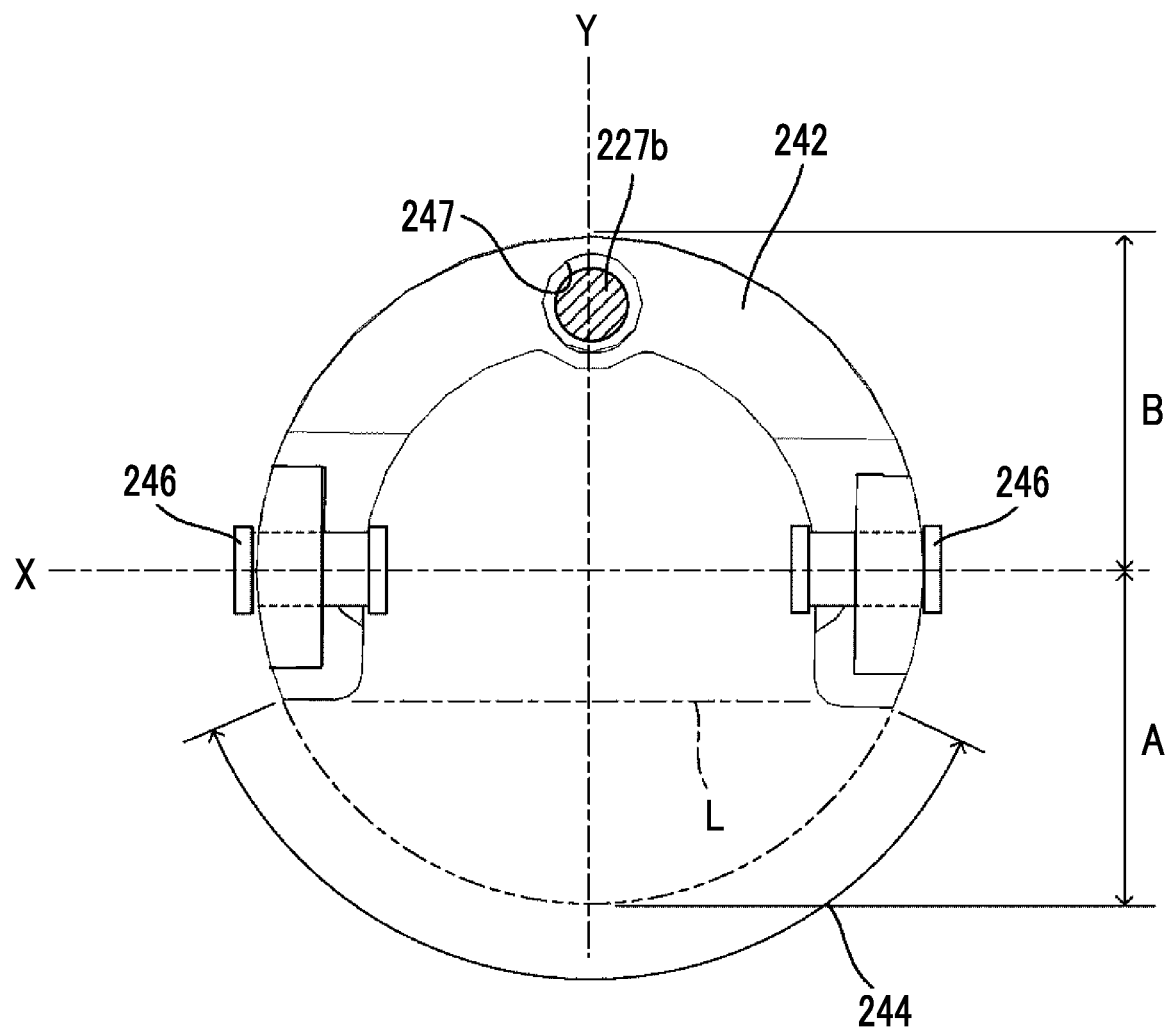
FIG. 30 is a view illustrating a configuration of the inside of the bending portion of FIG. 27.
Figure 31:
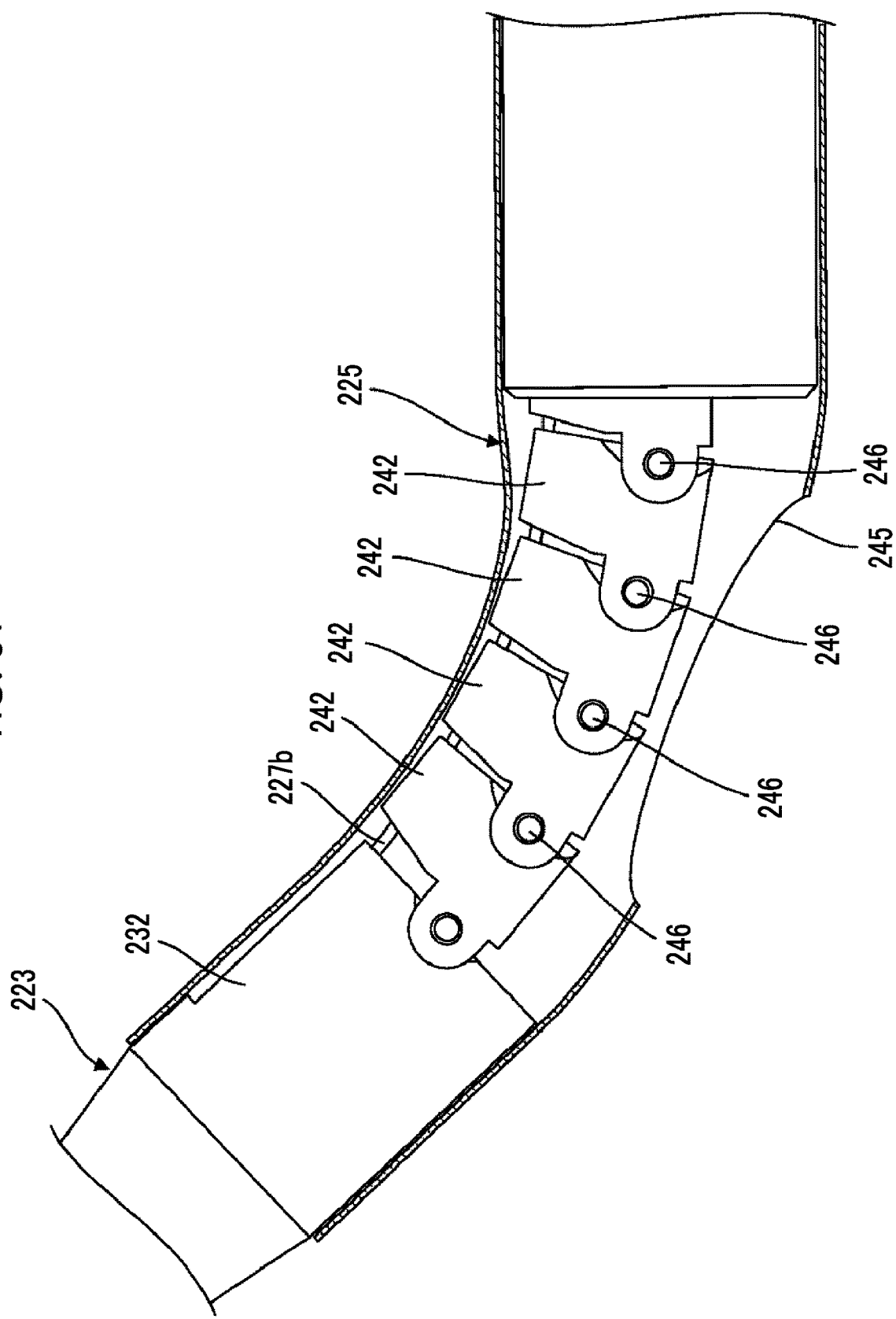
FIG. 31 is a view illustrating an operation inside the bending portion of FIG. 27.

FIGS. 29 to 31 illustrate a configuration and an operation of the inside of the bending portion 225.

The bending portion 225 has a plurality of bending pieces 242 and a resin outer coat 243. The plurality of bending pieces 242 are disposed to be arranged in a longitudinal direction of the insertion part 221 including the bending portion 225. Each of the plurality of bending pieces 242 is formed in a C-shape having a cutout portion 244, and the plurality of cutout portions 244 are also disposed to be arranged in the longitudinal direction of the insertion part 221. The outer coat 243 covers outer peripheries of the plurality of bending pieces 242 and configures the outer peripheral surface 225a of the bending portion 225. The outer coat 243 is provided with a hole 245, and the hole 245 is disposed to overlap the plurality of cutout portions 244.

Two adjacent bending pieces 242 are connected to each other via a pair of pins 246. The pair of pins 246 are disposed on the axis X that is substantially parallel to a line segment L which connects both ends of the cutout portions 244, and the two bending pieces 242 connected to each other by the pair of pins 246 are movable rotationally about the axis X which is a rotation axis. Although a configuration where the pair of pins on the rotation axis are used is adopted in this example, there may be one pin having a cantilevered configuration.

By adding rotational movements of the plurality of bending pieces 242 about the axis X which is a rotation axis, the bending portion 225 is bent into the predetermined curve shape, and the plurality of cutout portions 244 that are arranged in the longitudinal direction of the insertion part 221 are disposed outside the curve in the predetermined curve shape as illustrated in FIG. 31. The pipe line outlet 241 is configured by the plurality of cutout portions 244, and the opening 241a of the pipe line outlet 241 in the outer peripheral surface 225a is configured by the hole 245 of the outer coat 243. The outer coat 243 may be omitted and the plurality of bending pieces 242 may be exposed. In this case, the opening 241a of the pipe line outlet 241 is configured by the plurality of cutout portions 244.

The bending portion 225 is bent into the predetermined curve shape by an operation wire 227b. One end of the operation wire 227b is held by the distal end portion 223, and the operation wire 227b reaches the operation part 222 from the distal end portion 223 via the bending portion 225 and the connecting portion 226 and is pulled to the operation part 222 side or is pushed out to the distal end portion 223 side in response to operation of the operation part 222.

Each of the plurality of bending pieces 242 has a wire guide 247 that holds the operation wire 227b in a pushable and pullable manner. In a case where each of the bending pieces 242 is divided into two sides including the first side A, which includes the cutout portion 244, and the second side B, which is an opposite side, with the axis X as a boundary, the wire guide 247 is provided on the second side B. The operation wire 227b held by the plurality of wire guides 247 is held on the second side B and is disposed inside the curve in the predetermined curve shape. In this case, as the operation wire 227b is pulled to the operation part 222 side, the bending portion 225 is bent into the predetermined curve shape. In a case where the operation wire 227b is held on the first side A, the bending portion 225 is bent into the predetermined curve shape as the operation wire 227b is pushed out to the distal end portion 223 side.

Although all of the plurality of bending pieces 242 are connected to be movable rotationally about the axis X which is a rotation axis in this example, the bending portion 225 may have a bending piece connected to be movable rotationally about, for example, an axis Y perpendicular to the axis X which is a rotation axis. An operation wire which is held on at least one side in a case where the bending piece is divided into two with the axis Y as a boundary is provided. In addition, although a rotation axis passes through an approximate center of the bending piece in this example, the rotation axis may be biased in one direction. For example, in a case where the axis X of FIG. 30 is eccentrically disposed in a direction of the cutout portion 244, moment generated by pulling the operation wire 227b increases, and bending can be performed with a smaller force.

As the operation wire 227b is pulled to the operation part 222 side, the bending portion 225 is bent into the predetermined curve shape. In addition, as the operation wire 227a is pulled to the operation part 222 side, the grip portion 224 is closed. In this case, the operation wire 227a and the operation wire 227b are preferably the same operation wire. Accordingly, a closing operation of the grip portion 224 and a bending operation of the bending portion 225 can be performed by pulling the single operation wire, and thus operation of the operation part 222 is easy.

In a case where the operation wire 227a and the operation wire 227b are the same operation wire (hereinafter, referred to as an operation wire 227), the grip portion 224 is closed first as the operation wire 227 is pulled to the operation part 222 side. In a state where the grip portion 224 is closed, the bending portion 225 is configured to be bent into the predetermined curve shape. An operation sequence of the closing operation of the grip portion 224 and the bending operation of the bending portion 225 can be set depending on a relationship as to which one of an operation resistance in a case where the grip portion 224 is closed and an operation resistance in a case where the bending portion 225 bends into the predetermined curve shape is larger or smaller. In a case where the operation resistance of the bending portion 225 is relatively large, the closing operation of the grip portion 224 is performed first and then the bending operation of the bending portion 225 is performed.

The operation resistance in a case where the grip portion 224 is closed includes friction at the intersecting portion of the pair of grip claws 230 and friction at a connecting portion between the grip claw 230 and the link member 231. Similarly, the operation resistance in a case where the bending portion 225 bends into the predetermined curve shape includes friction at a connecting portion between the two bending pieces 242 adjacent to each other. In addition, the outer coat 243 of the bending portion 225 is an elastic member that extends the bending portion 225 in a straight line, and the operation resistance in a case where the bending portion 225 bends into the predetermined curve shape includes elasticity of the outer coat 243. The operation wire 227 is also an elastic member that extends the bending portion 225 in a straight line, and the operation resistance in a case where the bending portion 225 bends into the predetermined curve shape includes elasticity of the operation wire 227. The elastic member that extends the bending portion 225 in a straight line is not limited to the outer coat 243 and the operation wire 227, and may be a wire spring or a leaf spring.

Figure 32:
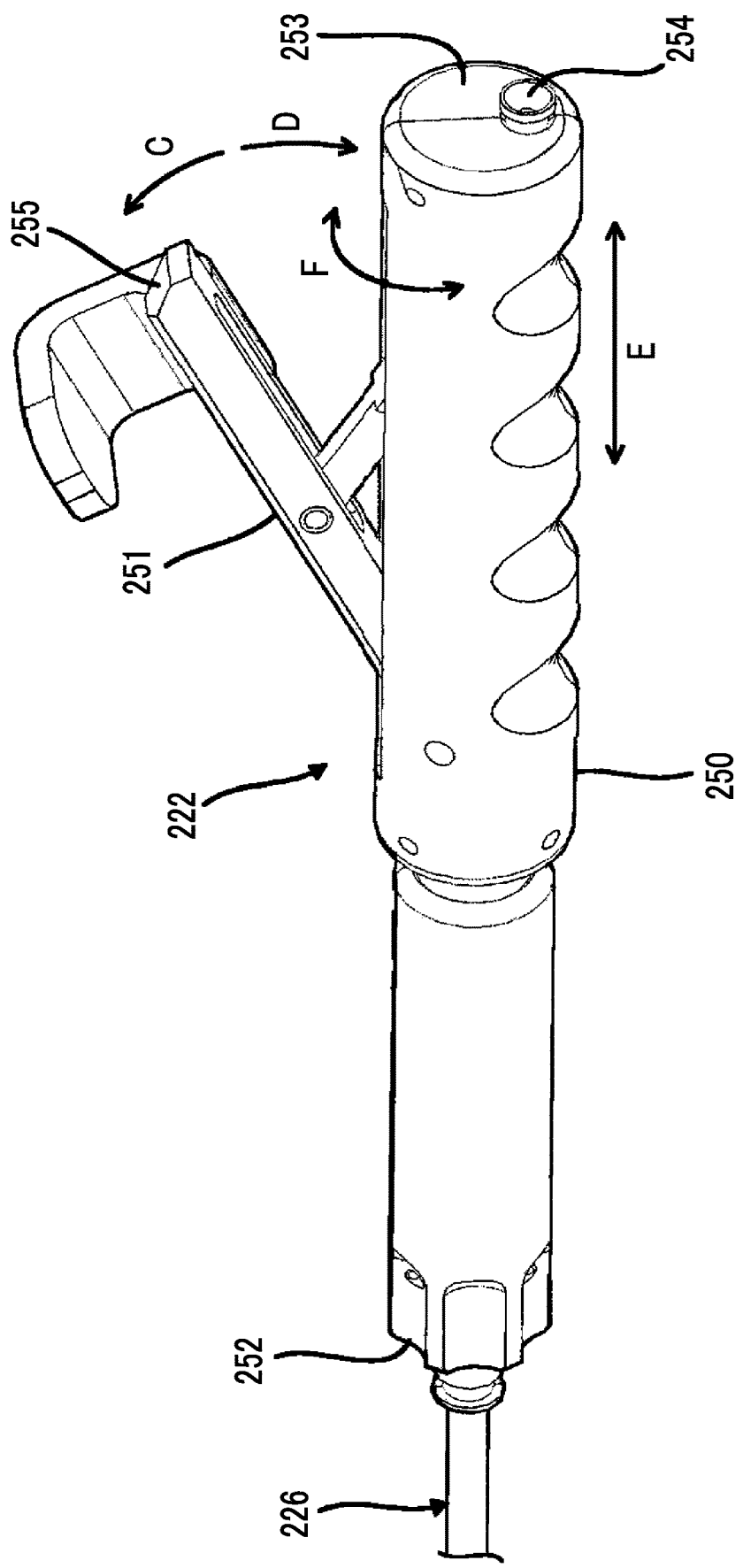
FIG. 32 is a view illustrating a configuration of an operation part of the endoscope treatment tool of FIG. 24.

FIG. 32 illustrates a configuration of the operation part 222. The operation wire 227a for closing the grip portion 224 and the operation wire 227b for bending the bending portion 225 into the predetermined curve shape will be described as the same operation wire.

The operation part 222 has an operation part body 250 and an operation handle 251. The operation part body 250 is formed in a rod shape, and the connecting portion 226 is connected to a distal end portion 252 of the operation part body 250. A treatment tool insertion opening 254 into which another endoscope treatment tool is insertable is provided in a proximal end portion 253 of the operation part body 250, and the treatment tool insertion opening 254 communicates with the pipe line 240 of the connecting portion 226 via the inside of the operation part body 250. The operation handle 251 is operably supported by the operation part body 250. The operation wire 227 is connected to the operation handle 251, and is pulled to the operation part 222 side and is pushed out to the distal end portion 223 side in response to an operation of the operation handle 251.

In this example, the operation handle 251 is swingably supported by the operation part body 250, and a free end portion 255 of the operation handle 251 is swingable in the opening direction C being spaced from the operation part body 250 and the closing direction D approaching the operation part body 250. The operation handle 251 is biased in the closing direction D by a biasing member (not illustrated) such as a spring. Herein, with respect to the swing of the operation handle 251 in the opening direction C, the operation wire 227 may be pulled to the operation part 222 side or may be pushed out to the distal end portion 223 side. However, preferably, the operation wire 227 is pushed out to the distal end portion 223 side with respect to the swing of the operation handle 251 in the opening direction C, and the operation wire 227 is pulled to the operation part 222 side with respect to the swing in the closing direction D. Since the operation handle 251 is biased in the closing direction D, the operation wire 227 is pulled in a state where the hand of the operator is separated from the operation handle 251, the grip portion 224 is kept in a closed state, and the bending portion 225 is kept in a state of being bent in the predetermined curve shape. It is desirable to adopt a configuration where a frictional force is generated by fastening the operation handle 251 from a side surface such that a position of the operation handle 251 is maintained with a constant force in a case where the operation of the operation handle 251 is stopped in a case where the operation handle 251 is not biased.

FIGS. 33 to 38 illustrate a treatment method for ESD as an example of a treatment method using the endoscope treatment tool 220. The operation wire 227 is pulled to the operation part 222 side with respect to the swing of the operation handle 251 in the closing direction D. In addition, another endoscope treatment tool used in combination with the endoscope treatment tool 220 is an incision tool, and is a high-frequency forcep 260 having a pair of openable and closable claws 261 at a distal end portion thereof. The pair of claws 261 are opened and closed by an operation part of the high-frequency forcep 260. In a state where the pair of claws 261 are closed and a living body tissue is gripped by the pair of claws 261, a high-frequency current flows between the pair of claws 261 and a return electrode plate via the living body tissue, or a high-frequency current flows between the pair of claws 261. Consequently, the living body tissue is cauterized and incision is performed.

The endoscope 202 is inserted into the body, and the endoscope distal end portion 210 is disposed at the side of the lesion part LA of a mucous membrane layer. The endoscope treatment tool 220 is inserted into the treatment tool channel 214 of the endoscope 202, and the distal end portion 223 and the bending portion 225 of the endoscope treatment tool 220 protrude from the end surface of the endoscope distal end portion 210. Then, the lesion part LA is gripped by the grip portion 224 of the distal end portion 223 through operation of the operation part 222 of the endoscope treatment tool 220.

Figure 33:
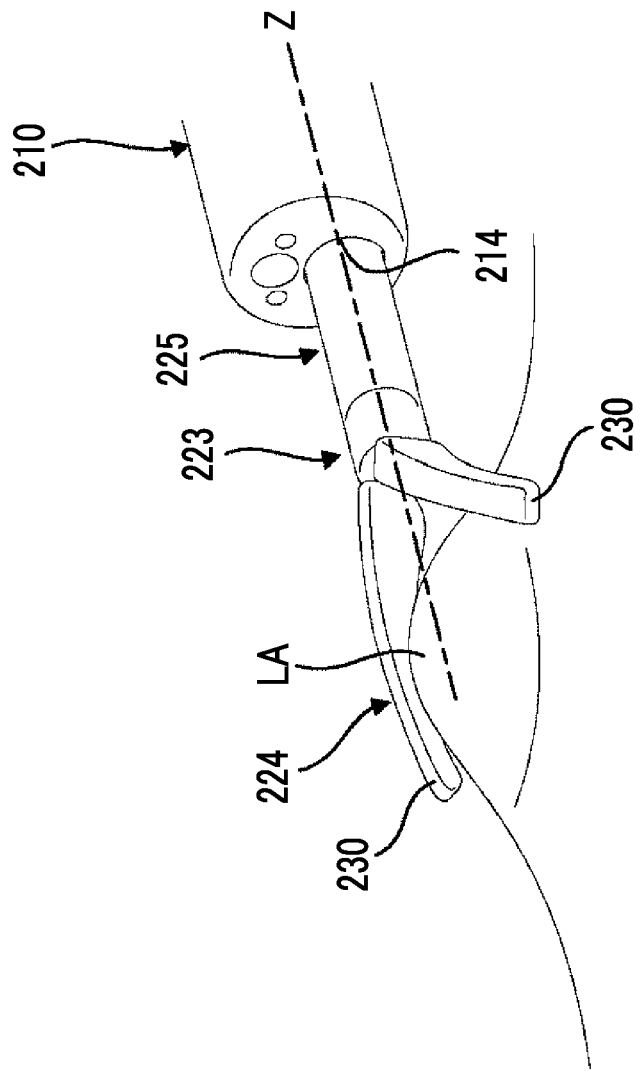
FIG. 33 is a view illustrating an example of a treatment method using the endoscope treatment tool of FIG. 24.

In a case where the lesion part LA is gripped by the grip portion 224, first, the operation handle 251 (refer to FIG. 32) of the operation part 222 is operated in the opening direction C. As illustrated in FIG. 33, the operation wire 227 is pushed out to the distal end portion 223 side in response to the operation of the operation handle 251. As the operation wire 227 is pushed out, the bending portion 225 is extended in a straight line and is laid along a longitudinal axis (the pipe axis Z of the pipe line 240) of the connecting portion 226. In addition, as the operation wire 227 is pushed out, the pair of grip claws 230 of the grip portion 224 are opened. Then, the operation part body 250 is pushed and pulled as appropriate, and the lesion part LA is disposed between the pair of grip claws 230.

Figure 34:
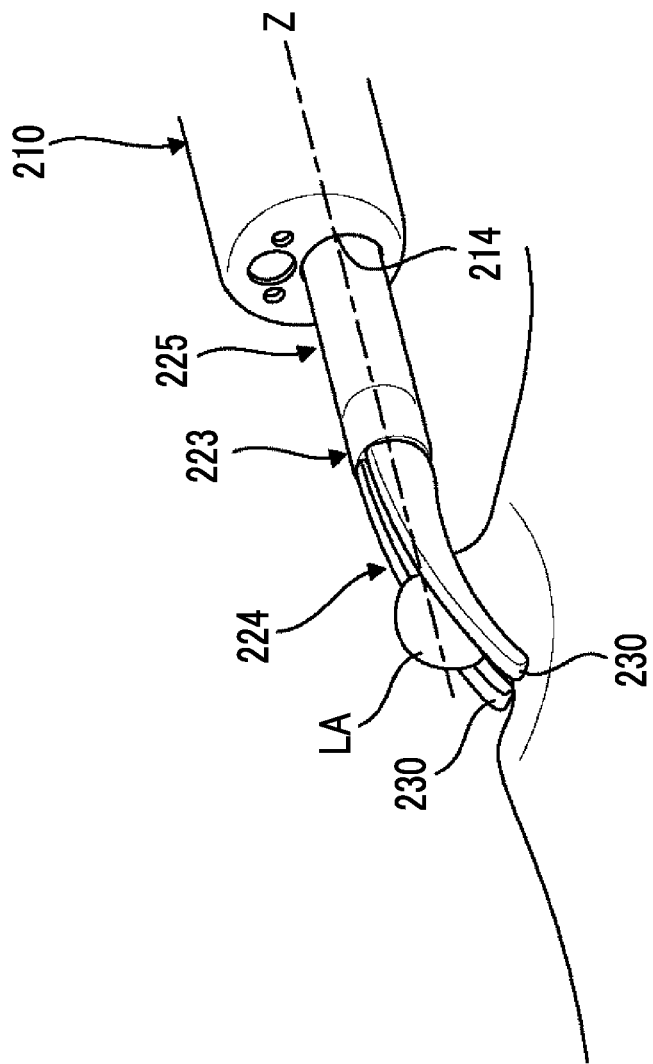
FIG. 34 is a view illustrating an example of the treatment method using the endoscope treatment tool of FIG. 24.
Figure 35:
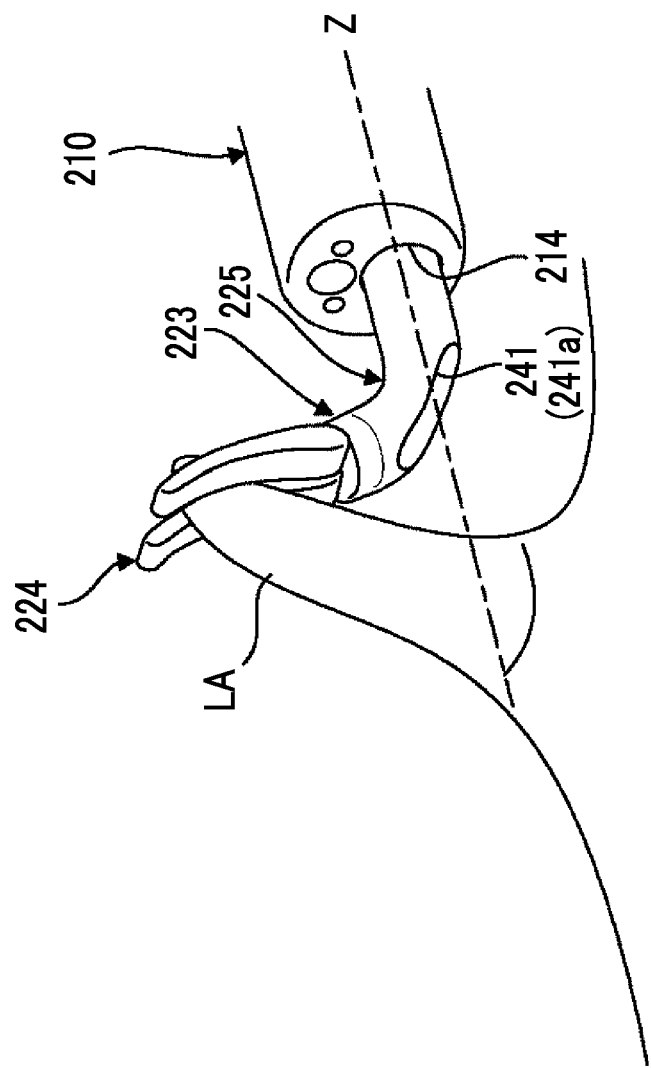
FIG. 35 is a view illustrating an example of the treatment method using the endoscope treatment tool of FIG. 24.

The hand of the operator separates from the operation handle 251 in a state where the lesion part LA is disposed between the pair of grip claws 230. The operation handle 251 is biased in the closing direction D, and swings in the closing direction D as the hand of the operator separates. Accordingly, the operation wire 227 is pulled to the operation part 222 side. As the operation wire 227 is pulled, the pair of grip claws 230 are closed first and the lesion part LA is gripped by the grip portion 224 as illustrated in FIG. 34. Then, after the lesion part LA is gripped by the grip portion 224, the bending portion 225 is bent into the predetermined curve shape as illustrated in FIG. 35. Accordingly, the grip portion 224 is erected from a state of being laid along the longitudinal axis (the pipe axis Z of the pipe line 240) of the connecting portion 226, and the lesion part LA gripped by the grip portion 224 is lifted.

Figure 36:
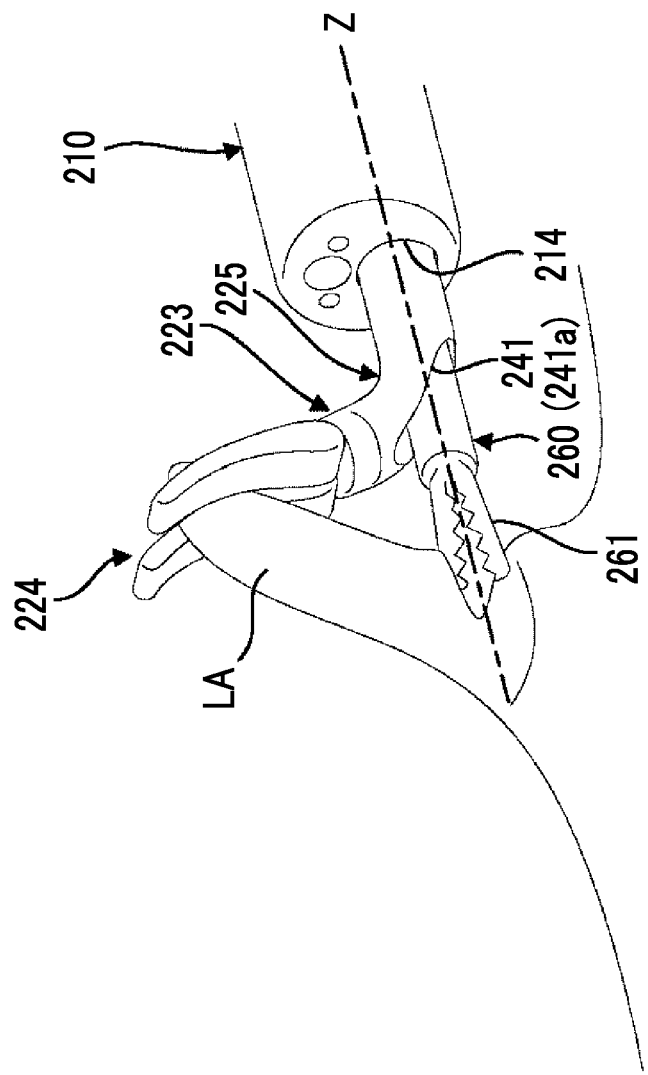
FIG. 36 is a view illustrating an example of a treatment method using a combination of the endoscope treatment tool of FIG. 24 and another endoscope treatment tool.

In a state where the lesion part LA is being lifted, the high-frequency forcep 260 inserted in the pipe line 240 of the connecting portion 226 protrudes from the pipe line outlet 241 as illustrated in FIG. 36. In a state where the bending portion 225 is bent in the predetermined curve shape, the opening 241a of the pipe line outlet 241 in the outer peripheral surface 225a of the bending portion 225 is disposed to intersect the pipe axis Z of the pipe line 240, and the high-frequency forcep 260 smoothly protrudes from the pipe line outlet 241 along the pipe axis Z. The opening 241a faces a position of the lesion part LA before being lifted, in other words, the lower part of the lifted lesion part LA, that is, faces an incision target in ESD, and the pair of claws 261 of the high-frequency forcep 260 protruding from the pipe line outlet 241 naturally reach the lower part of the lesion part LA. Then, the lower part of the lesion part LA is incised by the pair of claws 261 which have reached the lower part of the lesion part LA. As the incision proceeds, the lifted lesion part LA may be released once, re-gripped, and then lifted. In a case where the lesion part LA that has been once incised is lifted, the lower part is exposed so that the lower part is easily visible. Therefore, excision can be performed safely, reliably, and easily. The incision proceeds as the high-frequency forcep 260 is pushed and pulled as appropriate, and the lesion part LA including a submucosal layer is gradually peeled off.

In this manner, since the high-frequency forcep 260 can be disposed at the lower part of the lesion part LA through the pipe line 240 of the endoscope treatment tool 220 inserted in the treatment tool channel 214 of the endoscope 202, one treatment tool channel for the endoscope 202 is sufficient. Accordingly, it is possible to reduce a diameter of the endoscope 202.

In addition, since the lesion part LA can be lifted from the side of the lesion part LA only through operation of the operation handle 251 of the endoscope treatment tool 220, operation is simple. Then, as the lesion part LA is lifted from the side of the lesion part LA, the high-frequency forcep 260 can reach the lower part of the lesion part LA simply by making the high-frequency forcep 260 protrude from the pipe line outlet 241. Accordingly, lifting of the lesion part LA, exposing the lower part of the lesion part LA so as to be easily visible by lifting the lesion part LA, and accordingly treatment for the lower part of the lifted lesion part LA can be performed safely, reliably, and easily.

Further, since the lesion part LA can be kept in a lifted state even after the hand of the operator is separated from the operation handle 251 and thus the operator can concentrate on the operation of the high-frequency forcep 260 in a case of incision in this example, treatment for the lower part of the lesion part LA can be performed more easily by further simplifying the operation.

In a case of incision, the operation part body 250 of the operation part 222 may be pushed and pulled in the arrow E direction of FIG. 32 and/or the operation part body 250 may be rotated in the arrow F direction of FIG. 32. As described above, the connecting portion 226 has stiffness that allows translational and rotational power to be transmitted from the operation part 222 side to the bending portion 225 side, and pushing, pulling, and rotation of the operation part body 250 are transmitted to the bending portion 225 via the connecting portion 226.

Figure 37:
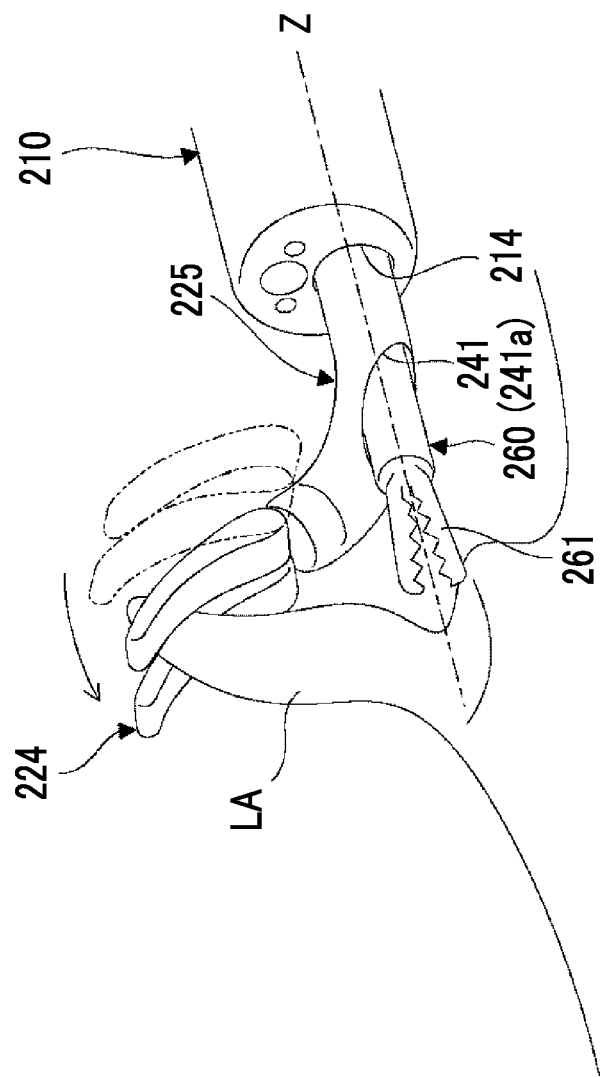
FIG. 37 is a view illustrating an example of a treatment method using a combination of the endoscope treatment tool of FIG. 24 and still another endoscope treatment tool.

FIG. 37 illustrates a case where the operation part body 250 is rotated. The connecting portion 226 is rotated about the longitudinal axis (the pipe axis Z of the pipe line 240) of the connecting portion 226 in response to the rotation of the operation part body 250. In a state where the bending portion 225 is bent in the predetermined curve shape, the grip portion 224 is rotated while keeping an erected state with respect to the longitudinal axis of the connecting portion 226, and the lesion part LA gripped by the grip portion 224 swings about the longitudinal axis of the connecting portion 226.

Figure 38:
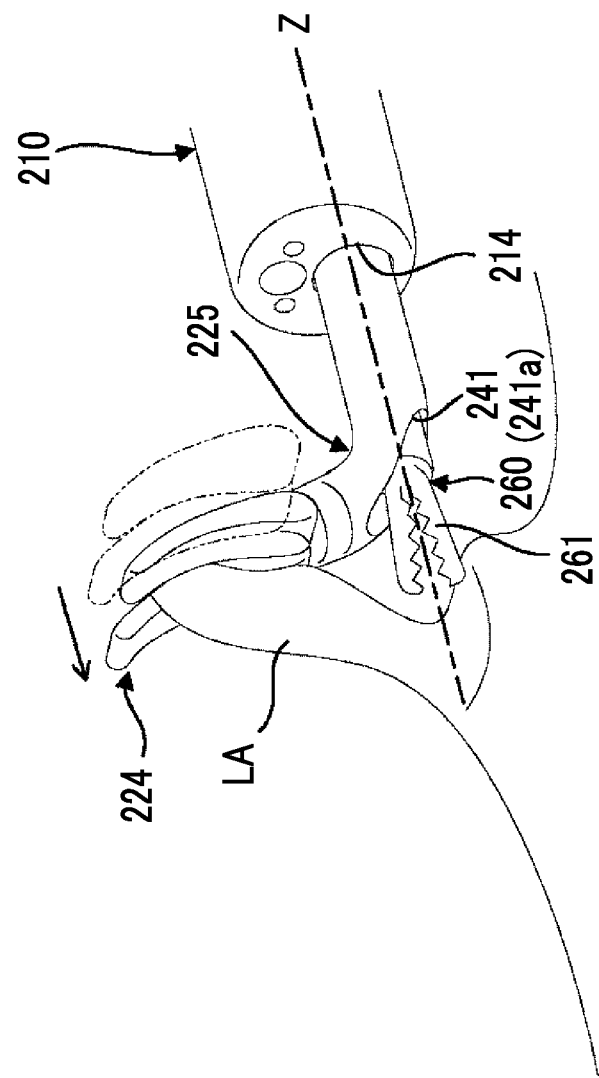
FIG. 38 is a view illustrating an example of a treatment method using a combination of the endoscope treatment tool of FIG. 24 and still another endoscope treatment tool.

FIG. 38 illustrates a case where the operation part body 250 is pushed and pulled. The connecting portion 226 is moved forward and backward in an axial direction of the longitudinal axis (the pipe axis Z of the pipe line 240) of the connecting portion 226 in response to the pushing and pulling of the operation part body 250. In a state where the bending portion 225 is bent in the predetermined curve shape, the grip portion 224 is moved forward and backward while keeping an erected state with respect to the longitudinal axis of the connecting portion 226, and the lesion part LA gripped by the grip portion 224 is pushed and pulled in the axial direction of the longitudinal axis of the connecting portion 226.

By swinging and/or pushing and pulling the lesion part LA as appropriate, for example, an incised wound can be widened. Accordingly, treatment for the lower part of the lesion part LA can be performed more easily.

Figure 39:
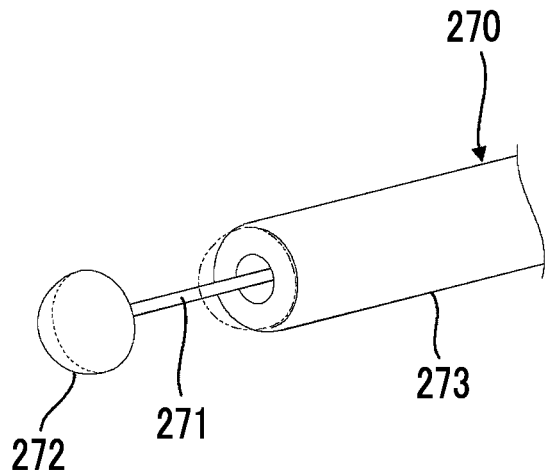
FIG. 39 is a schematic view illustrating another example of the endoscope treatment tool used in combination with the endoscope treatment tool of FIG. 2 and the endoscope treatment tool of FIG. 24.

Another endoscope treatment tool used in combination with the endoscope treatment tools 20 and 220 is not limited to the high-frequency forcep. For example, another endoscope treatment tool illustrated in FIG. 39 is a high-frequency knife which is an incision tool. This high-frequency knife 270 has a rod-shaped knife 271 at a distal end portion thereof, and is provided with an insulating tip 272 made of ceramics at a tip of the knife 271. The knife 271 is accommodated in a tubular sheath 273, and protrudes from the sheath 273 by an operation part of the high-frequency knife 270.

Figure 40:
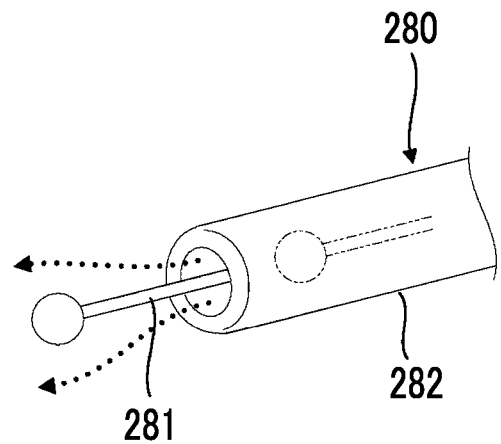
FIG. 40 is a schematic view illustrating still another example of the endoscope treatment tool used in combination with the endoscope treatment tool of FIG. 2 and the endoscope treatment tool of FIG. 24.

Another endoscope treatment tool illustrated in FIG. 40 is also a high-frequency knife which is an incision tool. This high-frequency knife 280 has a rod-shaped knife 281 at a distal end portion thereof. The knife 281 is accommodated in a tubular sheath 282, and protrudes from the sheath 282 by an operation part of the high-frequency knife 280. In addition, it is possible for a gas and a liquid to flow inside of the sheath 282. For example, cleaning water is sprayed from a distal end opening of the sheath 282 toward the knife 281. In addition, a body fluid such as blood is sucked from the distal end opening of the sheath 282.

Figure 41:
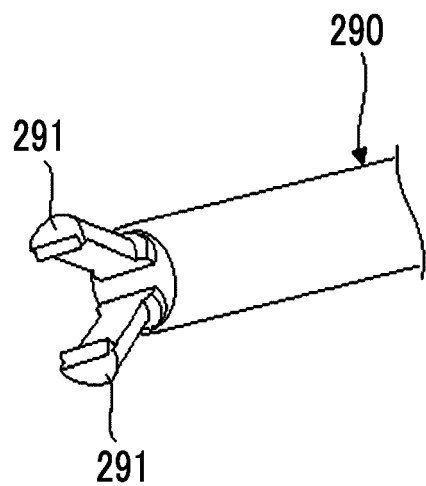
FIG. 41 is a schematic view illustrating still another example of the endoscope treatment tool used in combination with the endoscope treatment tool of FIG. 2 and the endoscope treatment tool of FIG. 24.

Another endoscope treatment tool illustrated in FIG. 41 is a bipolar hemostatic forcep that is a hemostatic tool. This bipolar hemostatic forcep 290 has a pair of openable and closable cups 291 at a distal end portion thereof and is opened or closed by an operation part (not illustrated). In a state where the pair of cups 291 are closed and a living body tissue is gripped by the pair of cups 291, high-frequency current flows between the pair of cups 291. Consequently, the living body tissue is cauterized and hemostasis is performed.

Figure 42:
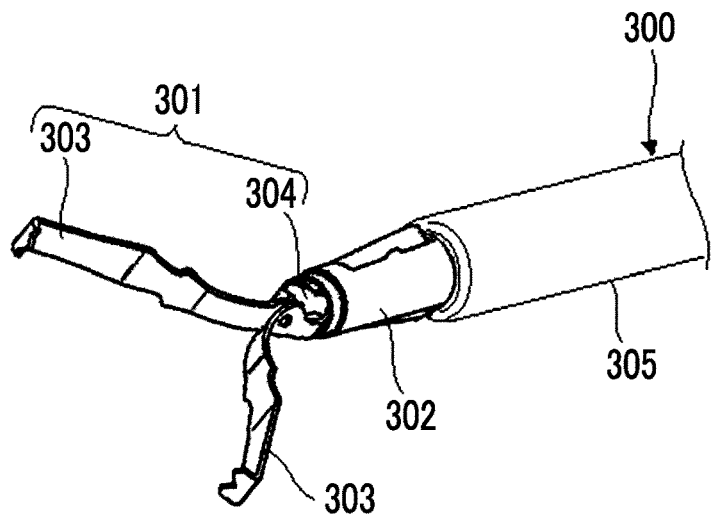
FIG. 42 is a schematic view illustrating still another example of the endoscope treatment tool used in combination with the endoscope treatment tool of FIG. 2 and the endoscope treatment tool of FIG. 24.

Another endoscope treatment tool illustrated in FIG. 42 is a clip that is a ligature tool (hemostatic tool). This clip 300 has a clip body 301 and a fastening ring 302 at a distal end portion thereof. The clip body 301 is made of an elastically deformable metal plate material, and has a pair of arm portions 303 and a connecting portion 304 that connects the pair of arm portions 303. The fastening ring 302 is mounted on an outer periphery of the connecting portion 304. In a case where the clip body 301 is pulled to an operation part side of the clip 300 via a wire (not illustrated), the fastening ring 302 that is stopped against a distal end of the sheath 305 is moved from the connecting portion 304 to outer peripheries of the pair of arm portions 303, and fastens the pair of arm portions 303. Accordingly, the pair of arm portions 303 are closed, and a living body tissue is ligated by the pair of arm portions 303. As the wire is further pulled, the clip body 301 comes off the wire, and the clip body 301 and the fastening ring 302 are placed at a part to be treated.

Figure 43:
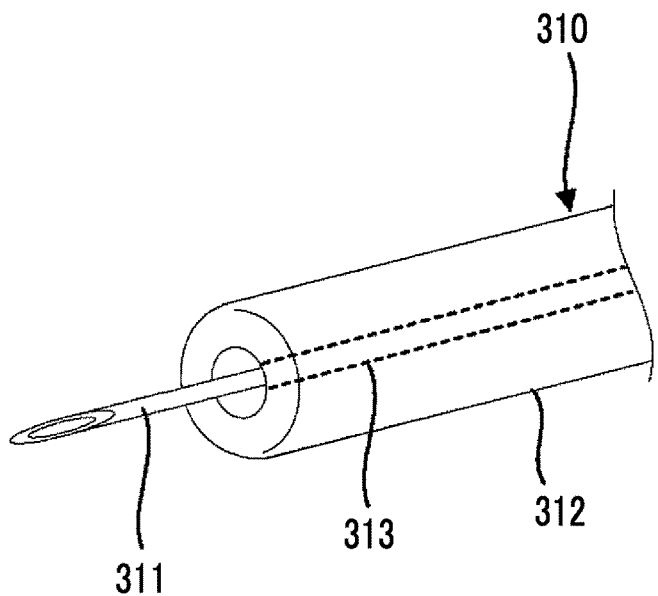
FIG. 43 is a schematic view illustrating still another example of the endoscope treatment tool used in combination with the endoscope treatment tool of FIG. 2 and the endoscope treatment tool of FIG. 24.

Another endoscope treatment tool illustrated in FIG. 43 is an injection needle. This injection needle 310 has a needle 311 at a distal end portion thereof. The needle 311 is accommodated in a tubular sheath 312, and protrudes from the sheath 312 by an operation part of the injection needle 310. A drug solution is supplied to the needle 311 from a syringe connected to the operation part of the injection needle 310 via a catheter 313 that is inserted in the sheath 312 and is connected to the needle 311.

Figure 44:
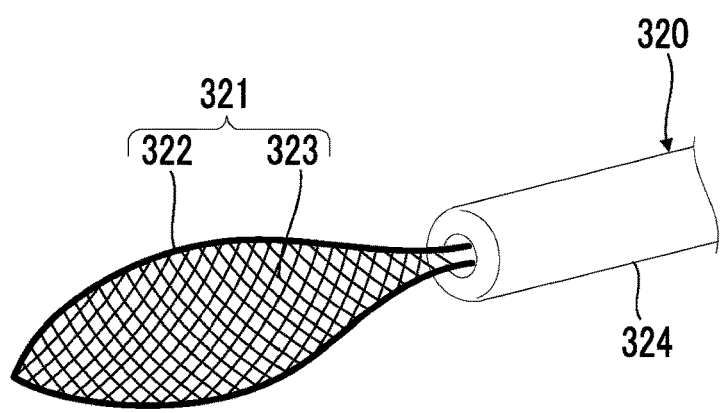
FIG. 44 is a schematic view illustrating still another example of the endoscope treatment tool used in combination with the endoscope treatment tool of FIG. 2 and the endoscope treatment tool of FIG. 24.

Another endoscope treatment tool illustrated in FIG. 44 is a collection net. This collection net 320 has a basket 321 at a distal end portion thereof. The basket 321 has a cyclic wire 322 which consists of an elastically deformable metal wire and a net 323 disposed inside the wire 322. The basket 321 is accommodated in a tubular sheath 324 in a closed state, and protrudes from the sheath 324 by an operation part of the collection net 320 to be opened by protruding.

Figure 45:
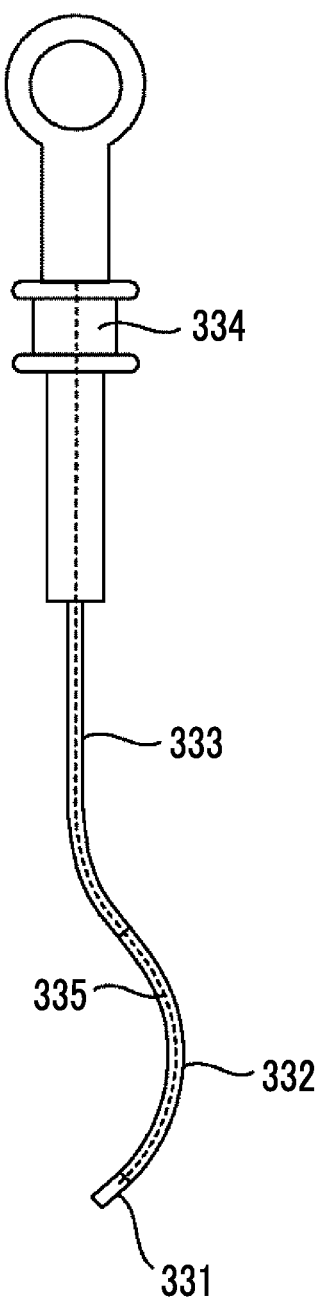
FIG. 45 is a schematic view illustrating still another example of the endoscope treatment tool used in combination with the endoscope treatment tool of FIG. 2 and the endoscope treatment tool of FIG. 24.

Another endoscope treatment tool such as the incision tool, the hemostatic tool, the injection needle, and the collection net that are listed above, may be a tool, in which a bending portion 332 is provided to be adjacent to an operation part side of a distal end portion 331 provided with a pair of claws and a knife and which is operated to be bent by an operation part, as in the example illustrated in FIG. 45. Similar to the bending portions 25 and 225 of the endoscope treatment tools 20 and 220, the bending portion 332 has a plurality of bending pieces and can be configured such that the two bending pieces adjacent to each other are connected to be movable rotationally. Then, an operation wire 335 that reaches an operation part 334 from the distal end portion 331 via the bending portion 332 and a connecting portion 333 is provided. As the operation wire 335 is pulled to an operation part 334 side or is pushed out to a distal end portion 331 side, the bending portion 332 is bent.

As described hereinbefore, the treatment tool disclosed in the present specification comprises an insertion part that is insertable into a body, an operation part, and a single operation wire that extends from the operation part to the insertion part and is pulled to an operation part side through the operation of the operation part. The insertion part includes a distal end portion that has an openable and closable grip portion, a bending portion that is able to be bent and is provided to be adjacent to the operation part side of the distal end portion, and a connecting portion that connects the bending portion to the operation part. The connecting portion is moved forward and backward along a longitudinal axis of the connecting portion and is rotated about the longitudinal axis of the connecting portion through operation of the operation part. As the connecting portion is moved forward and backward or is rotated, the grip portion moves forward and backward or rotates. As the operation wire is pulled, the grip portion is closed and the bending portion bends in a state where the grip portion is closed.

In addition, in the treatment tool disclosed in the present specification, the operation part has an operation state maintaining unit that maintains an operation state of at least one of forward and backward movement/rotation operation in which forward and backward movement and rotation of the grip portion are performed or opening/closing/bending operation in which opening and closing of the grip portion and bending of the bending portion are performed.

In addition, in the treatment tool disclosed in the present specification, an operation resistance when the bending portion bends based on pulling of the operation wire is larger than an operation resistance when the grip portion is closed based on the pulling of the operation wire.

In addition, in the treatment tool disclosed in the present specification, the bending portion has an elastic member that straightens the bending portion.

In addition, in the treatment tool disclosed in the present specification, the elastic member is an outer coat of the bending portion.

In addition, in the treatment tool disclosed in the present specification, the bending portion has a plurality of bending pieces that are arranged in a longitudinal direction of the insertion part and are connected to be movable rotationally.

In addition, in the treatment tool disclosed in the present specification, the bending portion is made of an elastic material and is flexible.

In addition, in the treatment tool disclosed in the present specification, the grip portion is erected from a state of being laid along the longitudinal axis of the connecting portion as the bending portion bends based on the pulling of the operation wire.

In addition, in the treatment tool disclosed in the present specification, when the connecting portion is rotated in a state where the bending portion is bent based on the pulling of the operation wire, the grip portion rotates while keeping an erected state with respect to the longitudinal axis of the connecting portion.

In addition, in the treatment tool disclosed in the present specification, when the connecting portion is moved forward and backward in a state where the bending portion is bent based on the pulling of the operation wire, the grip portion moves forward and backward while keeping an erected state with respect to the longitudinal axis of the connecting portion.

In addition, in the treatment tool disclosed in the present specification, the connecting portion has a pipe line, into which another treatment tool is insertable, therein, and the bending portion has a pipe line outlet that communicates with the pipe line and is open to an outer peripheral surface of the bending portion.

In addition, in the treatment tool disclosed in the present specification, based on the pulling of the operation wire, the bending portion bends into a curve shape in which the pipe line outlet is disposed outside a curve, and an opening of the pipe line outlet is disposed to intersect the pipe axis of the pipe line, in the curve shape.

In addition, in the treatment tool disclosed in the present specification, each of the plurality of bending pieces is formed in a C-shape having a cutout portion, and the cutout portion of each of the plurality of bending pieces is disposed outside the curve in the curve shape and configures the pipe line outlet.

In addition, the treatment tool disclosed in the present specification comprises an insertion part that is insertable into a body and an operation part. The insertion part includes a distal end portion that has a grip portion which opens and closes through operation of the operation part and a bending portion that is provided to be adjacent to an operation part side of the distal end portion and bends through the operation of the operation part, and a connecting portion that connects the bending portion to the operation part. The connecting portion has a pipe line, into which another endoscope treatment tool is insertable, therein. The bending portion has a pipe line outlet that communicates with the pipe line and is open to an outer peripheral surface of the bending portion.

In addition, in the treatment tool disclosed in the present specification, through the operation of the operation part, the bending portion bends into a curve shape in which the pipe line outlet is disposed outside a curve, and an opening of the pipe line outlet is disposed to intersect a pipe axis of the pipe line, in the curve shape.

In addition, in the treatment tool disclosed in the present specification, the bending portion has a plurality of bending pieces that are arranged in a longitudinal direction of the insertion part and are connected to be movable rotationally, each of the plurality of bending pieces is formed in a C-shape having a cutout portion, and the cutout portion of each of the plurality of bending pieces is disposed outside the curve in the curve shape and configures the pipe line outlet.

In addition, the treatment tool disclosed in the present specification comprises a single operation wire that reaches the distal end portion from the operation part via the connecting portion and the bending portion and is disposed inside the curve in the curve shape. As the operation wire is pulled to the operation part side, the grip portion is closed, and the bending portion bends into the curve shape in a state where the grip portion is closed.

In addition, in the treatment tool disclosed in the present specification, an operation resistance in a case where the bending portion bends into the curve shape is larger than an operation resistance in a case where the grip portion is closed.

In addition, in the treatment tool disclosed in the present specification, the bending portion has an elastic member that extends the bending portion in a straight line.

In addition, in the treatment tool disclosed in the present specification, the elastic member is an outer coat of the bending portion.

In addition, in the treatment tool disclosed in the present specification, the grip portion is erected from a state of being laid along the longitudinal axis of the connecting portion as the bending portion bends into the curve shape.

In addition, in the treatment tool disclosed in the present specification, when the connecting portion is rotated about the longitudinal axis of the connecting portion in a state where the bending portion is bent in the curve shape, the grip portion rotates while keeping an erected state with respect to the longitudinal axis of the connecting portion.

In addition, in the treatment tool disclosed in the present specification, when the connecting portion is moved forward and backward along the longitudinal axis of the connecting portion in a state where the bending portion is bent in the curve shape, the grip portion moves forward and backward while keeping an erected state with respect to the longitudinal axis of the connecting portion.

In addition, the endoscope device disclosed in the present specification comprises a first treatment tool that is the treatment tool described above, a second treatment tool, and an endoscope that has a first treatment tool channel into which the first treatment tool is insertable and a second treatment tool channel into which the second treatment tool is insertable.

In addition, the endoscope device disclosed in the present specification comprises a first treatment tool that is the treatment tool described above, a second treatment tool, an endoscope that has a treatment tool channel into which one treatment tool of the first treatment tool or the second treatment tool is insertable, and a guide sheath that has a treatment tool channel into which the other treatment tool of the first treatment tool or the second treatment tool is insertable and an endoscope channel into which the endoscope is insertable.

In addition, the endoscope device disclosed in the present specification comprises a first treatment tool that is the treatment tool described above, a second treatment tool that is insertable into the pipe line of the first treatment tool, and a treatment tool channel into which the first treatment tool is insertable.

In addition, in the endoscope device disclosed in the present specification, at least one of the first treatment tool or the second treatment tool is attachable to and detachable from an endoscope operation part that performs operation of the endoscope.

In addition, the endoscope system disclosed in the present specification comprises the endoscope device, a light source device that supplies illumination light to the endoscope of the endoscope device, and a processor that processes an image signal output from the endoscope.

In addition, in the treatment method disclosed in the present specification, the distal end portion of the first treatment tool is disposed at a lesion part in a body through the first treatment tool channel of the endoscope by using the endoscope device, the lesion part is gripped by the grip portion of the first treatment tool, the lesion part is lifted as the bending portion of the first treatment tool is bent in a state where the lesion part is gripped, and a lower part of the lesion part is treated by the second treatment tool inserted in the second treatment tool channel of the endoscope in a state where the lesion part is lifted.

In addition, in the treatment method disclosed in the present specification, the distal end portion of the first treatment tool is disposed at a lesion part in a body through one treatment tool channel of the treatment tool channel of the endoscope or the treatment tool channel of the guide sheath by using the endoscope device, the lesion part is gripped by the grip portion of the first treatment tool, the lesion part is lifted as the bending portion of the first treatment tool is bent in a state where the lesion part is gripped, and a lower part of the lesion part is treated by the second treatment tool inserted in the other treatment tool channel of the treatment tool channel of the endoscope or the treatment tool channel of the guide sheath in a state where the lesion part is lifted.

In addition, in the treatment method disclosed in the present specification, the distal end portion of the first treatment tool is disposed at a lesion part in a body through the treatment tool channel of the endoscope by using the endoscope device, the lesion part is gripped by the grip portion of the first treatment tool, the lesion part is lifted as the bending portion of the first treatment tool is bent in a state where the lesion part is gripped, and a lower part of the lesion part is treated by the second treatment tool inserted in the pipe line of the first treatment tool, in a state where the lesion part is lifted.

In addition, in the treatment method disclosed in the present specification, the lesion part is swung as the connecting portion is rotated about a longitudinal axis of the connecting portion of the first treatment tool in a state where the lesion part is lifted.

In addition, in the treatment method disclosed in the present specification, the lesion part is pushed and pulled as the connecting portion is moved forward and backward along the longitudinal axis of the connecting portion of the first treatment tool in a state where the lesion part is lifted.

EXPLANATION OF REFERENCES

1: endoscope system
2: endoscope
3: light source device
4: processor
5: monitor
6: endoscope insertion part
7: endoscope operation part
8: universal cord
9: connector
10: endoscope distal end portion
11: endoscope bending portion
12: endoscope connecting portion
13: first treatment tool insertion opening
14: first treatment tool channel
15: second treatment tool insertion opening
16: second treatment tool channel
20: endoscope treatment tool
21: insertion part
22: operation part
23: distal end portion
24: grip portion
25: bending portion
26: connecting portion
27: operation wire
30: grip claw
31: link member
32: support body
33: pin
42: bending piece
43: outer coat
46: pin
47: wire guide
50: operation part body
51: operation handle
52: attachment part
53: proximal end portion of operation part body
54: treatment tool insertion opening
55: shaft
56: slider
57: link
58: maintaining unit
58a to 58d: friction member
59: maintaining unit
60: high-frequency forcep (second treatment tool)
61: pair of claws
101: endoscope system
102: endoscope
103: guide sheath 104: endoscope channel
105: treatment tool channel
106: endoscope insertion part
107: endoscope operation part
108: universal cord
109: connector
110: endoscope distal end portion
111: endoscope bending portion
112: endoscope connecting portion
113: treatment tool insertion opening
114: treatment tool channel
201: endoscope system
202: endoscope
203: light source device
204: processor
205: monitor
206: endoscope insertion part
207: endoscope operation part
208: universal cord
209: connector
210: endoscope distal end portion
211: endoscope bending portion
212: endoscope connecting portion
213: treatment tool insertion opening
214: treatment tool channel
220: endoscope treatment tool
221: insertion part
222: operation part
223: distal end portion
224: grip portion
225: bending portion
225a: outer peripheral surface
226: connecting portion
227: operation wire
227a: operation wire
227b: operation wire
230: grip claw
231: link member
232: support body
233: pin
240: pipe line
241: pipe line outlet
241a: opening
242: bending piece
243: outer coat
244: cutout portion
245: hole
246: pin
247: wire guide
250: operation part body
251: operation handle
252: distal end portion of operation part body
253: proximal end portion of operation part body
254: treatment tool insertion opening
255: free end portion of operation handle
260: high-frequency forcep (second treatment tool)
261: pair of claws
A: first side
B: second side
C: opening direction
D: closing direction
E: arrow
F: arrow
L: line segment
LA: lesion part
X: axis
Y: axis
Z: pipe axis

What is claimed is:

1. A treatment tool comprising:
an insertion part that is insertable into a body;
an operation part; and
a single operation wire that extends from the operation part to the insertion part and is pulled to an operation part side through operation of the operation part,
wherein the insertion part includes
a distal end portion that has an openable and closable grip portion,
a bending portion that is provided to be adjacent to the operation part side of the distal end portion and is able to be bent, and
a connecting portion that connects the bending portion to the operation part,
the connecting portion is moved forward and backward along a longitudinal axis of the connecting portion and is rotated about the longitudinal axis of the connecting portion, through the operation of the operation part,
as the connecting portion is moved forward and backward or is rotated, the grip portion moves forward and backward or rotates, and
as the operation wire is pulled, the grip portion is closed, and the bending portion bends in a state where the grip portion is closed,
wherein the operation part comprises an operation part body and an operation handle swingably supported by the operation part body, and the operation wire is pulled through a swing of the operation handle with respect to the operation part body,
wherein the operation part has an operation state maintaining unit that maintains an operation state of forward and backward movement/rotation operation in which forward and backward movement and rotation of the grip portion are performed and opening/closing/bending operation in which opening and closing of the grip portion and bending of the bending portion are performed.

2. The treatment tool according to claim 1,
wherein an operation resistance when the bending portion bends based on pulling of the operation wire is larger than an operation resistance when the grip portion is closed based on the pulling of the operation wire.

3. The treatment tool according to claim 2,
wherein the bending portion has an elastic member that straightens the bending portion.

4. The treatment tool according to claim 3,
wherein the elastic member is an outer coat of the bending portion.

5. The treatment tool according to claim 1,
wherein the bending portion has a plurality of bending pieces that are arranged in a longitudinal direction of the insertion part and are connected to be movable rotationally.

6. The treatment tool according to claim 1,
wherein the bending portion consists of an elastic material and is flexible.

7. The treatment tool according to claim 1,
wherein as the bending portion bends based on pulling of the operation wire, the grip portion is erected from a state of being laid along the longitudinal axis of the connecting portion.

8. The treatment tool according to claim 7,
wherein when where the connecting portion is rotated in a state where the bending portion is bent based on the pulling of the operation wire, the grip portion rotates while keeping an erected state with respect to the longitudinal axis of the connecting portion.

9. The treatment tool according to claim 7,
wherein when the connecting portion is moved forward and backward in a state where the bending portion is bent based on the pulling of the operation wire, the grip portion moves forward and backward while keeping an erected state with respect to the longitudinal axis of the connecting portion.

10. The treatment tool according to claim 1,
wherein the connecting portion has a pipe line, into which another treatment tool is insertable, therein, and
the bending portion has a pipe line outlet that communicates with the pipe line and is open to an outer peripheral surface of the bending portion.

11. The treatment tool according to claim 10,
wherein based on pulling of the operation wire, the bending portion bends into a curve shape in which the pipe line outlet is disposed outside a curve, and
in the curve shape, an opening of the pipe line outlet is disposed to intersect a pipe axis of the pipe line.

12. An endoscope device comprising:
a first treatment tool that is the treatment tool according to claim 10;
a second treatment tool that is insertable into the pipe line of the first treatment tool; and
an endoscope that includes a treatment tool channel into which the first treatment tool is insertable.

13. A treatment method comprising:
using the endoscope device according to claim 12;
disposing the distal end portion of the first treatment tool at a lesion part in a body through the treatment tool channel of the endoscope;
gripping the lesion part by the grip portion of the first treatment tool;
lifting, in a state where the lesion part is gripped, the lesion part by bending the bending portion of the first treatment tool; and
treating, in a state where the lesion part is lifted, a lower part of the lesion part by the second treatment tool inserted in the pipe line of the first treatment tool.

14. The treatment tool according to claim 1,
wherein the bending portion has a plurality of bending pieces that are arranged in a longitudinal direction of the insertion part and are connected to be movable rotationally,
wherein the connecting portion has a pipe line, into which another treatment tool is insertable, therein, and
the bending portion has a pipe line outlet that communicates with the pipe line and is open to an outer peripheral surface of the bending portion,
wherein based on pulling of the operation wire, the bending portion bends into a curve shape in which the pipe line outlet is disposed outside a curve, and
in the curve shape, an opening of the pipe line outlet is disposed to intersect a pipe axis of the pipe line,
wherein each of the plurality of bending pieces is formed in a C-shape having a cutout portion, and
the cutout portion of each of the plurality of bending pieces is disposed outside the curve in the curve shape and forms the pipe line outlet.

15. An endoscope device comprising:
a first treatment tool that is the treatment tool according to claim 1;
a second treatment tool; and
an endoscope that has a first treatment tool channel into which the first treatment tool is insertable and a second treatment tool channel into which the second treatment tool is insertable.

16. The endoscope device according to claim 15,
wherein at least one of the first treatment tool or the second treatment tool is attachable to and detachable from an endoscope operation part that performs operation of the endoscope.

17. An endoscope system comprising:
the endoscope device according to claim 15;
a light source device that supplies illumination light to the endoscope of the endoscope device; and
a processor that processes an image signal output from the endoscope.

18. A treatment method comprising:
using the endoscope device according to claim 15;
disposing the distal end portion of the first treatment tool at a lesion part in a body through the first treatment tool channel of the endoscope;
gripping the lesion part by the grip portion of the first treatment tool;
lifting, in a state where the lesion part is gripped, the lesion part by bending the bending portion of the first treatment tool; and
treating, in a state where the lesion part is lifted, a lower part of the lesion part by the second treatment tool inserted in the second treatment tool channel of the endoscope.

19. The treatment method according to claim 18,
wherein as the connecting portion is rotated about a longitudinal axis of the connecting portion of the first treatment tool in a state where the lesion part is lifted, the lesion part is swung.

20. The treatment method according to claim 18,
wherein as the connecting portion is moved forward and backward along a longitudinal axis of the connecting portion of the first treatment tool in a state where the lesion part is lifted, the lesion part is pushed and pulled.

21. An endoscope device comprising:
a first treatment tool that is the treatment tool according to claim 1;
a second treatment tool;
an endoscope that has a treatment tool channel into which one treatment tool of the first treatment tool or the second treatment tool is insertable; and
a guide sheath that has a treatment tool channel into which the other treatment tool of the first treatment tool or the second treatment tool is insertable and an endoscope channel into which the endoscope is insertable.

22. A treatment method comprising:
using the endoscope device according to claim 21;
disposing the distal end portion of the first treatment tool at a lesion part in a body through one treatment tool channel of the treatment tool channel of the endoscope or the treatment tool channel of the guide sheath;
gripping the lesion part by the grip portion of the first treatment tool;
lifting, in a state where the lesion part is gripped, the lesion part by bending the bending portion of the first treatment tool; and treating, in a state where the lesion part is lifted, a lower part of the lesion part by the second treatment tool inserted in the other treatment tool channel of the treatment tool channel of the endoscope or the treatment tool channel of the guide sheath.

* * * * *